(12) United States Patent
Miethke et al.

(10) Patent No.: US 11,696,779 B2
(45) Date of Patent: Jul. 11, 2023

(54) PERICARDIAL GRIPPER AND METHOD OF IMPLANTING A TEMPORARY CARDIAC ASSIST SYSTEM

(71) Applicant: Christoph Miethke GmbH & Co KG, Potsdam (DE)

(72) Inventors: Christoph Miethke, Potsdam (DE); Lucas Thieme, Berlin (DE); Tim Klettnig, Potsdam (DE)

(73) Assignee: Christoph Miethke GmbH & Co KG, Potsdam (DE)

( * ) Notice: Subject to any disclaimer, the term of this patent is extended or adjusted under 35 U.S.C. 154(b) by 488 days.

(21) Appl. No.: 16/645,409

(22) PCT Filed: Oct. 10, 2018

(86) PCT No.: PCT/EP2018/000468
§ 371 (c)(1),
(2) Date: Mar. 6, 2020

(87) PCT Pub. No.: WO2019/072412
PCT Pub. Date: Apr. 18, 2019

(65) Prior Publication Data
US 2020/0281614 A1    Sep. 10, 2020

(30) Foreign Application Priority Data

Oct. 12, 2017 (DE) ..................... 10 2017 009 488.8

(51) Int. Cl.
*A61B 17/30* (2006.01)
*A61B 17/34* (2006.01)
(Continued)

(52) U.S. Cl.
CPC .......... *A61B 17/30* (2013.01); *A61B 17/3468* (2013.01); *A61M 60/148* (2021.01);
(Continued)

(58) Field of Classification Search
CPC .............. A61B 17/22031; A61B 17/30; A61B 17/3421; A61B 17/00247;
(Continued)

(56) References Cited

U.S. PATENT DOCUMENTS 5,830,191 A  11/1998 Hildwein et al.
6,544,216 B1  4/2003 Sammler et al.
(Continued)

FOREIGN PATENT DOCUMENTS

DE  102008018919 A1  10/2009
EP     1956963 A1   8/2008
(Continued)

OTHER PUBLICATIONS

Maisch et al., "Guideline on the Diagnosis and Management of Pericardial Diseases", European Heart Journal, 2004.
(Continued)

*Primary Examiner* — Majid Jamialahmadi
(74) *Attorney, Agent, or Firm* — Smartpat PLC

(57) ABSTRACT

A method for gripping the pericardium uses a device with an outer part and an inner part. The device is pushed through an incision towards the pericardium until an end of the device touches the pericardium or the heart or a layer arranged on the heart. Subsequently, the inner part is moved until at least one outer part end and/or an inner part end is arranged on the pericardium. The device for gripping the pericardium has an inner tube and an outer tube. The inner tube and the outer tube have end surfaces with different surface structures.

14 Claims, 12 Drawing Sheets

(51) Int. Cl.
*A61M 60/148* (2021.01)
*A61B 17/00* (2006.01)

(52) U.S. Cl.
CPC ............... *A61B 2017/00247* (2013.01); *A61B 2017/306* (2013.01)

(58) Field of Classification Search
CPC ........ A61B 17/00243; A61B 2017/306; A61B 2017/00347; A61B 2017/3425; A61B 17/3423; A61B 17/3468
See application file for complete search history.

(56) References Cited

U.S. PATENT DOCUMENTS

| | | | |
|---|---|---|---|
| 9,585,689 B2 | 3/2017 | Kobayashi | |
| 2003/0093104 A1* | 5/2003 | Bonner | A61B 17/3478 606/185 |
| 2005/0165324 A1* | 7/2005 | Receveur | A61N 1/056 600/549 |
| 2010/0016663 A1 | 1/2010 | Maisch et al. | |
| 2010/0249490 A1 | 9/2010 | Farnan | |
| 2011/0022168 A1 | 1/2011 | Cartledge | |
| 2011/0098806 A1 | 4/2011 | Otto et al. | |
| 2015/0080664 A1 | 3/2015 | Kobayashi | |
| 2015/0105627 A1 | 4/2015 | Kobayashi | |
| 2017/0027611 A1* | 2/2017 | Adams | A61B 17/42 |
| 2017/0143322 A1 | 5/2017 | Muse et al. | |
| 2019/0038820 A1 | 2/2019 | Granegger et al. | |

FOREIGN PATENT DOCUMENTS

| | | |
|---|---|---|
| JP | 2012515624 A | 7/2012 |
| JP | 2014004015 A | 1/2014 |
| JP | 2014176720 A | 9/2014 |
| JP | 2017124109 A | 7/2017 |
| WO | 2013190967 A1 | 12/2013 |
| WO | 2013190968 A1 | 12/2013 |
| WO | 2016025850 A1 | 2/2016 |
| WO | 2017134304 A1 | 8/2017 |

OTHER PUBLICATIONS

Sarah Zubke, "Entwicklung eines Herzbeutel Zugangs für die Einbringung eines das Herz unterstützenden Implantats", Masterarbeit, Fachgebiet Medizintechnik, Technische Universität Berlin, 2017.

* cited by examiner

Fig. 1
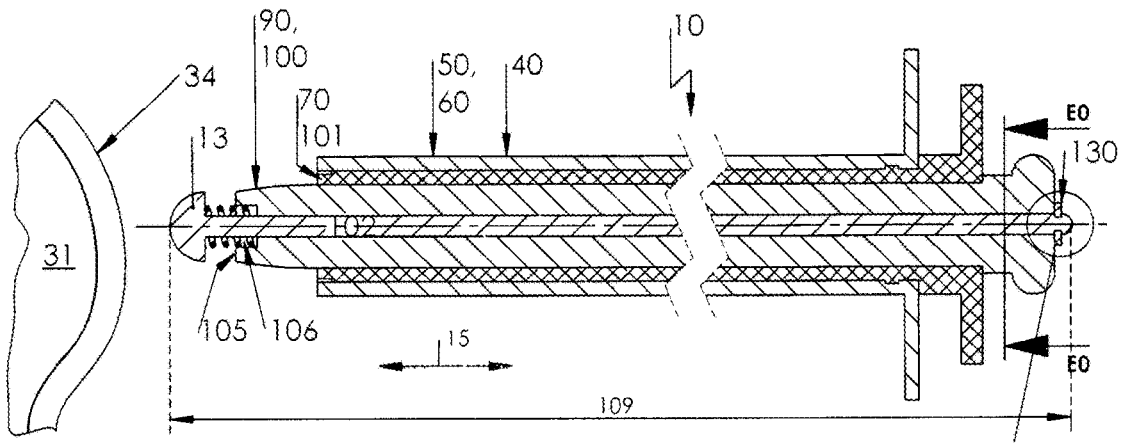
Fig. 1a
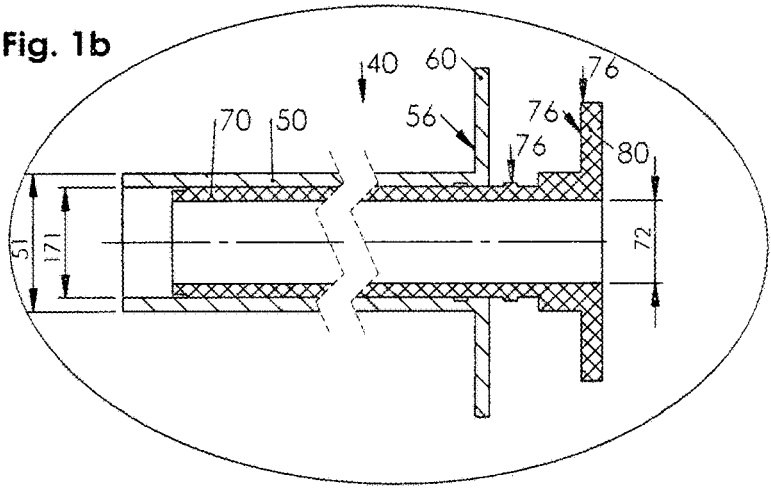
Fig. 1b
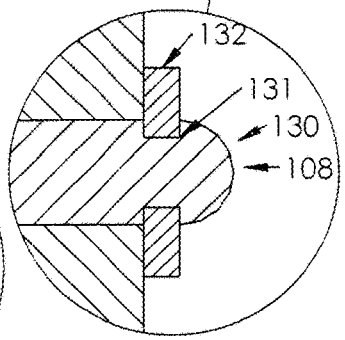
Fig. 1d
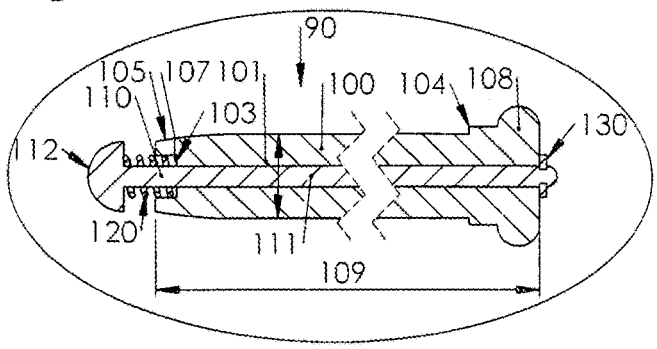
Fig. 1c
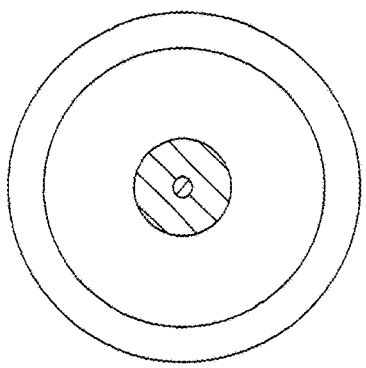
Fig. 1e
E0 - E0

Fig. 2
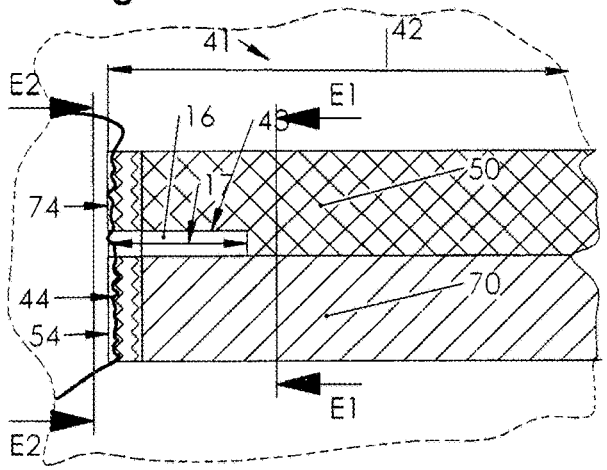
Fig. 2a
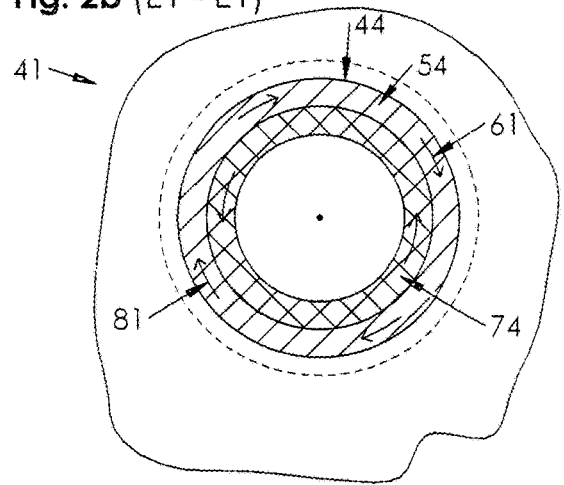
Fig. 2b (E1 - E1)
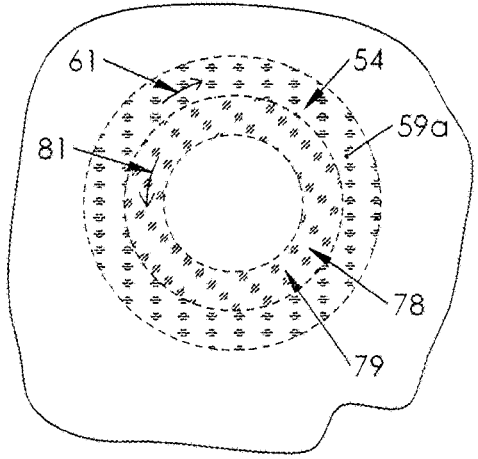
Fig. 2c (E2 - E2)

Fig. 3
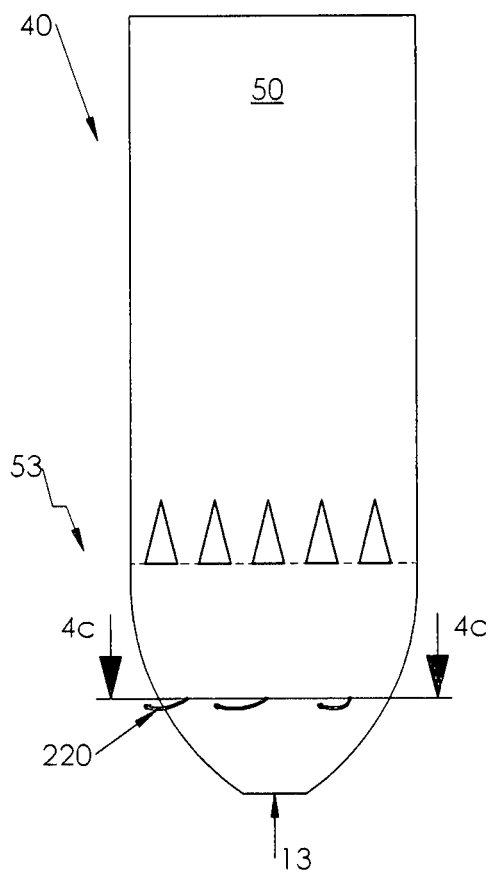
Fig. 3a
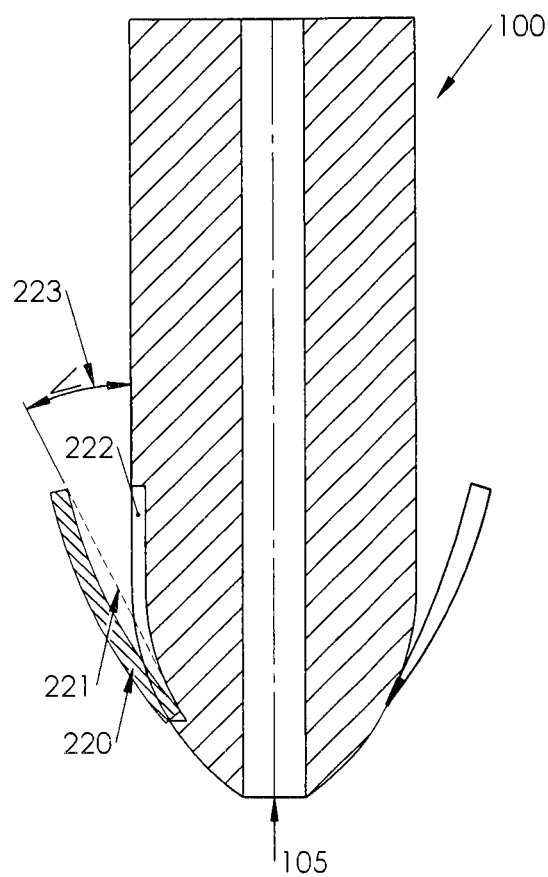
Fig. 3b
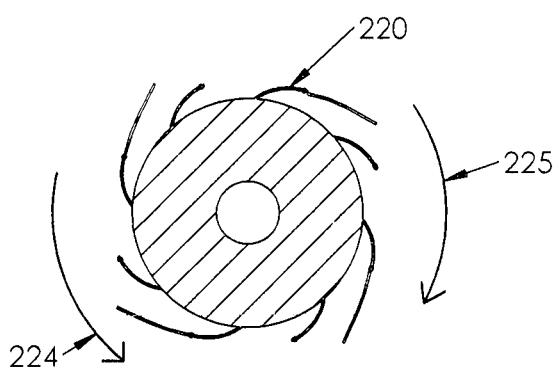
Fig. 3c

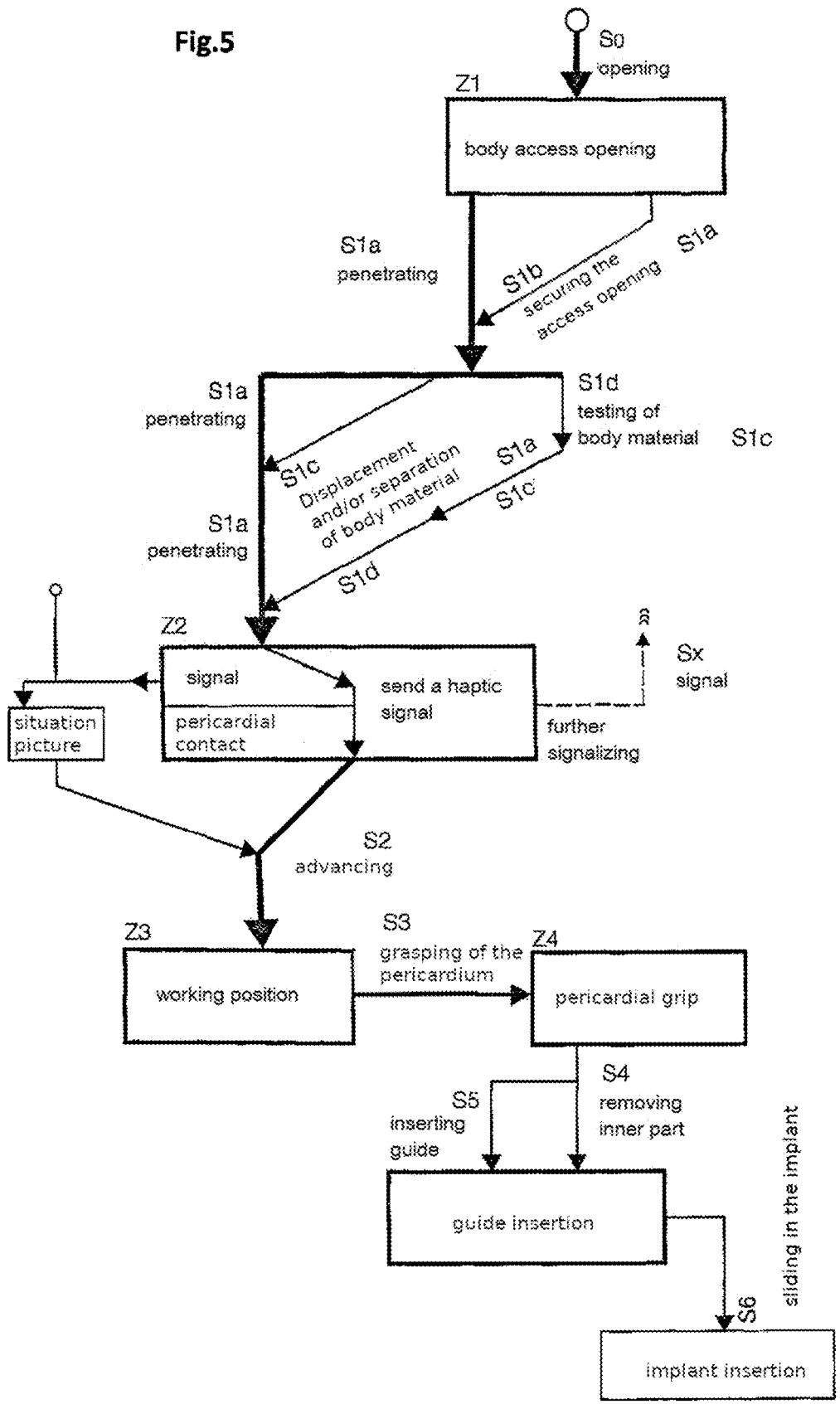

Fig. 6
Fig. 6a
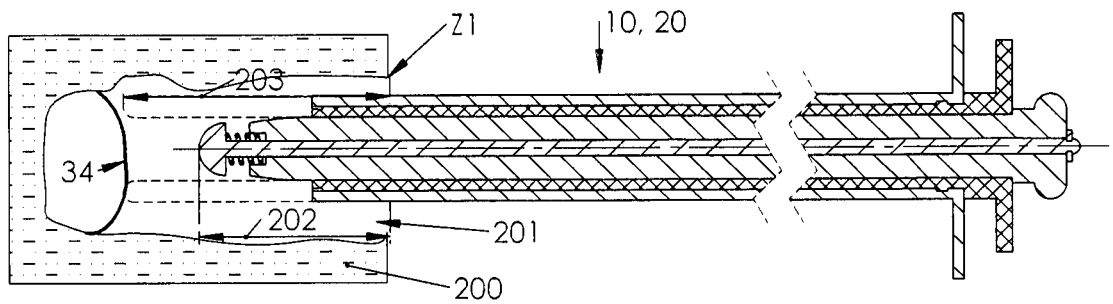
Fig. 6b
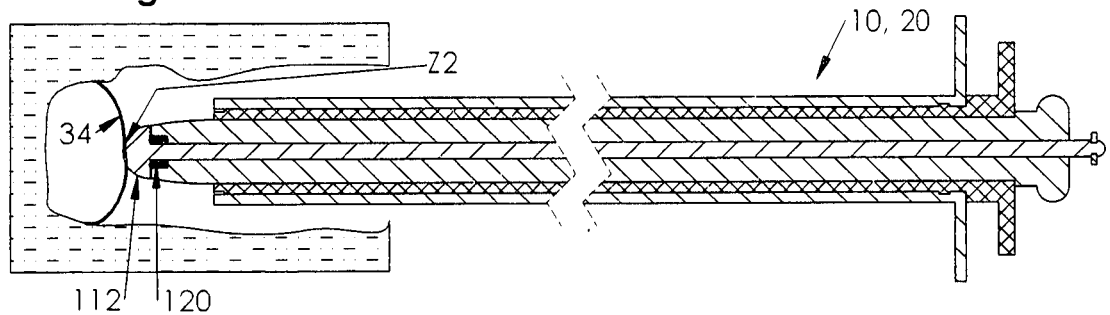
Fig. 6c
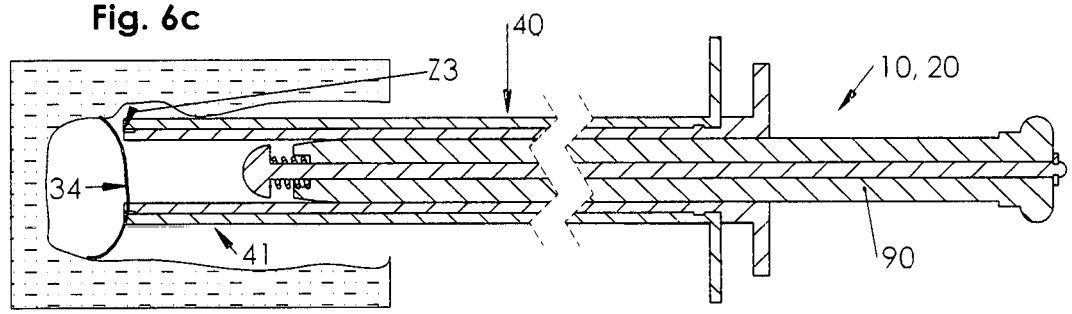
Fig. 6d
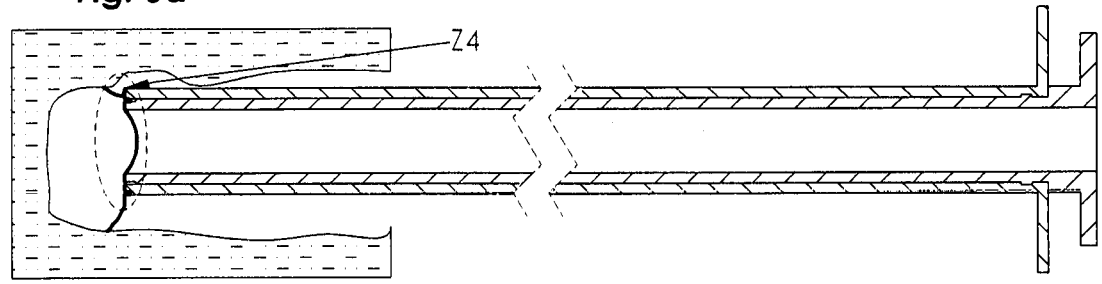

Fig. 11
Fig. 11a
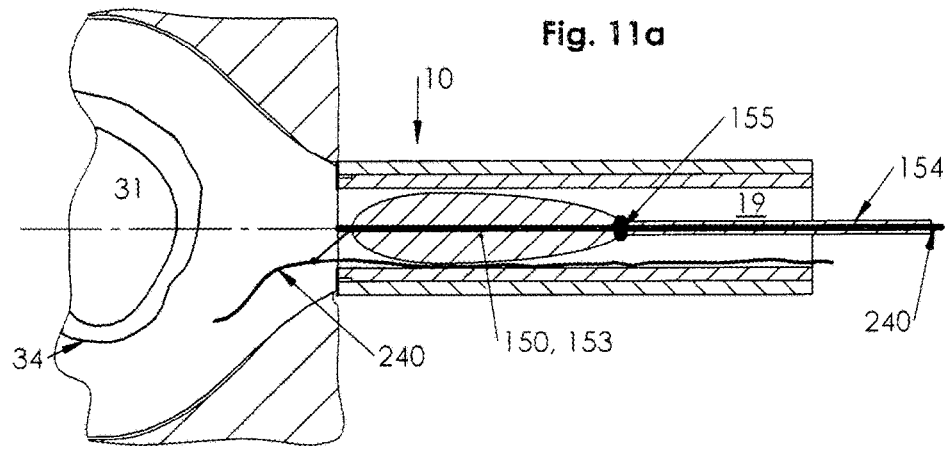
Fig. 11b
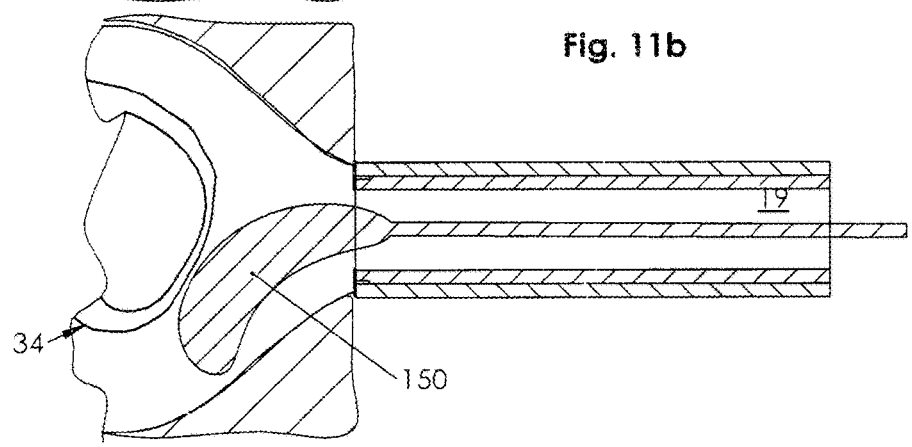
Fig. 11c
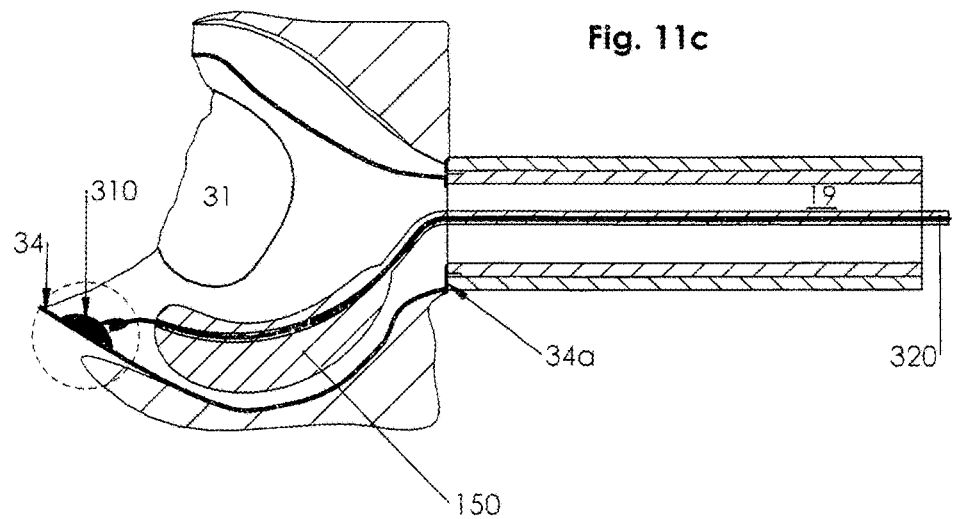

PERICARDIAL GRIPPER AND METHOD OF IMPLANTING A TEMPORARY CARDIAC ASSIST SYSTEM

TECHNICAL FIELD

The disclosure relates to a method for gripping the pericardium using at least one device which comprises at least one outer part and at least one inner part.

BACKGROUND

The heart is a necessary organ for the viability of different species. The human species also uses its periodic contracting and relaxing, beating, for pumping blood through its body. Science models its service as a positive-displacement pump and parameterizes its rhythm therein as the opening and closing of valve flaps in order to understand its operation.

Cardiology is the science of the heart's activity in structure and function, as well as of its activity in interaction with other organs. It also includes dysfunctions of the heart. As a result of aging, treatment or disease, the heart's ability to beat may be reduced. Causes of this so-called cardiac insufficiency may be high blood pressure, heart valve defects or calcification of coronary vessels.

In her master's thesis: "Entwicklung eines Herzbeutel Zugangs für die Einbringung eines das Herz unterstützenden Implantats" ("Development of a pericardium access for the insertion of a heart-supporting implant"), autumn 2017, Department of Medical Technology, Technical University of Berlin (Reference 1), Sarah Zubke explains the basics of cardiac insufficiency.

According to her work, terminologically, insufficiencies are defined according to the European Society of Cardiology by differentiating three forms, the so-called: systolic and diastolic insufficiency as well as cardiac insufficiency with middle left ventricular ejection fraction. According to the work of Ms. Zubke, in 2014, according to the Federal Statistical Office of Germany, about 430,000 patients with cardiac insufficiency were recorded wherein about 36,000 died of it.

Today, a lot of measures are used to treat cardiac insufficiency. Known elements of this set, sequenced along a scale, are: heart transplantation, pacemakers or drugs. The sequence decreases with the severity of cardiac insufficiency.

Therapy with cardiac support is also an element that may be sequenced along the scale next to the element heart transplantation. Both elements differ in the criterion of their duration of use. Cardiac support therapies are configured to last for hours or days, whereas heart transplantation-based therapies last for months or years.

With regard to cardiac support, the state of the art includes: intra-aortic balloon blood pumps, percutaneous intravascular pumping systems—so-called blood pumps or percutaneous sheathing devices.

U.S. Pat. No. 6,544,216 B1 teaches an intracardiac blood pump. It has a tube-like embodiment, its first end in the right atrium and its second end in the pulmonary artery—operated through the pulmonary heart valve. One section of its tube-like embodiment includes a pumping section. Therefore, the intracardiac blood pump pumps blood from the right atrium into the pulmonary artery during surgery.

Blood flows through the pumping section, enters it radially at the first end, but leaves it axially at the second end.

Because blood flows through the pump section, surface effects occur between individual blood cell surfaces and internal pump section surfaces. These surface effects, for example friction, damage the blood cells. A disadvantage of the intracardiac blood pump is therefore its blood cell-damaging effect.

In WO 2017/134304 A1 a technique of a pump supported by passive magnetic action is described. This blood pump delivers fluid from its inlet to its outlet by building up a delivery pressure. The pressure force of the delivery pressure overcomes a closing force closing the blood pump.

The sealing force results from a passive magnetic bearing of the rotor in the blood pump, whereby the rotor is at least passively magnetically attracted or repelled axially in one direction. Because it is magnetically attracted or repelled, the rotor is forced into a seat.

The compressive force results from the transfer of rotational energy by means of blades from the rotor to the blood surrounding it. As it rotates, blood is scooped in one direction—a flow of blood—and pushed forward.

The blood pump pumps when the direction of the pressure force opposes the direction of the sealing force and is greater in strength.

The blades do not only touch the blood, but their rotational speed creates friction between the surfaces of the blood lines and the blade surfaces. Thus, they endanger the blood cells.

A market participant describes on her webpage http://www.cardiobridge.com/technology/ on Sep. 14, 2017 a technology called "10E-Reitan Catheter". According to her own information, this is a subcutaneous and intra-arterial short term intraaortic percutaneous circulatory support. In operation, the product is inserted into the pulmonary artery and is spaced apart from the heart. The product consists of a wire net stretched over a propeller in which a propeller rotates. The wire net balloons the surrounding section of the pulmonary artery. The propeller lies in the wire net at right angles to the direction of blood flow. Its rotation thus accelerates the blood flow by transferring kinetic energy to it. The higher the transfer of kinetic energy, the higher the substitution of the heart's pumping capacity.

However, the propeller is in direct contact with the blood, resulting in the destruction of blood cells.

All blood pumps presented here have the disadvantage in common that they damage, usually destroy, blood cells. This disadvantage is known in the state of the art as the so-called haemolysis rate. It describes the ratio of destroyed to non-destroyed blood cells or pumped blood volume.

The EP 10 2008 018 919 A1 suggests a sheathing device to support and/or take over the pumping function of the heart. This is intended to apply directed cyclical compression and decompression to the heart in cases of need, for example during acute cardiac insufficiency, in order to support the heart's pumping action. The idea behind applying the directed cyclical compression and decompression is to enclose the heart with a mantle whose mantle volume is compressible. Its volume changes are then applied to the heart surface as a directed force. To grasp it, it requires the mantle to be inserted into the patient. This condition is further elaborated in the proposal, in which the compressibility of the mantle is used to make the conembodiment device foldable. This embodiment is less invasive and less demanding.

Its essential functional requirement to encase the heart is its essential disadvantage. A sheathing in case of need means a sheathing under time pressure and under unfavourable conditions. In practice, both make it difficult to apply the conembodiment device correctly.

In the state of the art, various aids are known which are available to a person treating a patient, for example, a doctor treating cardiac insufficiency. A variety of assistive devices help the physician in an operation to move medical devices such as blood pumps to their destination in the human body.

Known aids are scalpels, cannulas or forceps.

Scalpels are very sharp blades. They are guided by the doctor by hand and force hand-guided, free-form incisions. If a scalpel is used to reach a deep-seated destination in the human body, an exposed blade must be guided through the body by the doctor.

Its sharp blade is a disadvantage of the scalpel. It exposes the human body to the risk of dangerous cuts.

Cannulas are medical needles, including hollow needles and hypodermic needles. They are preferably used to inject liquids into or withdraw liquids from the human body. They are inserted into the body by pushing them through the skin, internal membranes, tissues, tissue sections, organs. This advance is made possible and facilitated because the needle tip is sharp, usually ground.

Its sharp needle tip is also a disadvantage of the cannula. If the cannula is advanced too deeply into the body—for example beyond its destination—important parts of the body are injured unintentionally, sometimes unnoticed.

Medical forceps help the doctor to hold on to body parts. If they are gripped incorrectly or too tightly, they have the disadvantage of tearing tissues.

The anatomy differentiates the heart from its surrounding pouch. This pouch is called the heart pouch, in the doctor's terminology the pericardium.

An overview of pericardial diseases is given in the ESC Guideline "Guideline on the Diagnosis and Management of Pericardial Diseases", European Heart Journal 2004.

A minimal opening of the pericardium, its punctual piercing or puncturing is called pericardial puncture. It differentiates the so-called wet from dry puncturing. For this purpose, the presence or absence of a fluid or fluid cushion between the heart and the pericardium, in lingua medicus effusion, is the criterion.

If an effusion is present so that a physician punctures the effusion from the outside through the pericardium, the physician punctures wet. If there is no effusion, i.e. the pericardium is close to or on the heart, the physician punctures dry.

Today the heart is treated mechanically if the pericardium may be punctured wet. This is the case when the effusion fills an approximate minimum volume of about 25 ml, because this minimum volume compensates for a possible misalignment of a treatment tool—a cannula or needle—by the treating physician. The effusion therefore protects against a certain degree of slipping, slipping off or misalignment in the moment of the puncture.

Therefore, when puncturing, an X-ray imaging technique is usually used, firstly to visually follow the advance of the treatment tool, and secondly to detect the moment of puncture.

For this purpose, e.g. when using a needle, an X-ray contrast medium is applied through the tip. This forms a liquid point in front of the needle tip within a tissue, at the moment of puncture, and a veil in the cavity of the pericardium. If a liquid point melts into a veil, it is possible to distinguish in the X-ray image whether the pericardium is punctured or not.

In EP 1 956 963 B1 an arrangement for guiding instruments is explained. As examples of instruments, it refers to endoscopes, removal or assembly tools or tools for optical imaging of selected areas in cavities. The arrangement is intended to particularly enable instruments to be guided relative to at least part of the walls of a cavity in general, and medical or veterinary instruments to be guided in cavities in living organisms. It solves the special case by segmenting the arrangement so that it is a link chain whose joints are connected to each other in a manner that allows them to be bent and the length of individual segments or several connected segments to be varied. Because of this solution, there is the benefit in making it possible for the first time: defined examinations, reliable punctures or other manipulations.

According to an online innovation report, "Marburger-Attacher revolutionizes pericardial puncture", dated 9 Mar. 2005 on a subpage of the website "www.innovation-report.de", the so-called Marburger-Attacher enables a user to "perform targeted and signal-monitored minimally invasive manipulation of organs".

The Marburger-Attacher embodiments the phenomenon for puncturing the pericardium in a protected space, by a volume that is cut into one of its ends, into which pericardium is sucked, so that by holding it, due to this suction force, the pericardium may be turned away from the heart in order to puncture it safely.

Creating a protected space for a puncture is complex. Providing such a space results in providing its volume. This makes the Marburger-Attacher large and unwieldy.

In summary, the state of the art knows of mechanisms of action that are based on suction of the pericardium.

The disadvantage of the state of the art is that it requires a more invasive access to the heart.

In U.S. Pat. No. 9,585,689 B2 a teaching of an access—an airlock is published. This offers a defined passage generally through a biological membrane, —and in detail through the pericardium. As an outer part, the airlock comprises two tubes inserted into each other and an inner part guided in the outer part. It is pushed into a puncture, because in a first step it is punctured with a needle, in a second step a wire is passed through it, and in a third step: inner part, inner and outer tube, —the airlock were passed over the wire, because the wire is tunnelled through the airlock. The initial pushing of the airlock into the puncture is followed by the fixation of the pericardium in the airlock. A distance between the inner and outer tube may be reduced since the inner tube may be retracted axially against the direction of advance. A reduction results in a contraction of the groove because this distance describes a groove width. The groove will pinch the pericardium surrounding the puncture when the groove is reduced because the groove is intended to be in the puncture.

Use of the airlock requires a pericardial puncture. Unfortunately, the airlock has no functionality to puncture the pericardium, so the puncture must be performed with a second tool. Introducing a second tool into the human body is introducing a second source of contamination. This results in a disadvantage of the closest state of the art, it increases the risk of infection.

The use of the airlock also requires its fixation. Since this is the result of pericardial entrapment in a groove, the airlock must be manipulated by a treating person until the groove is in the puncture. Manipulation in the confinement and darkness of the human body through a minimally invasive incision is complicated and endangers the success of the therapy due to this complexity.

After using the airlock, it must be removed from the human body. The airlock must be pulled, regularly. Pulling out the sheath causes the puncture to tear open because pericardium is in the groove when the sheath is used correctly.

SUMMARY

The object of the disclosure is to create a gentle introduction of medical devices into human cavities. It is solved by a method for gripping the pericardium with at least one device, the device comprising at least one outer part and at least one inner part, in which a body opening is created, wherein the device is advanced through the body opening in the direction of the pericardium until at least one end of the device touches the pericardium or the heart or a layer arranged on the heart, so that then the inner part is moved until at least one outer part end and/or inner part end is located at the pericardium, the object is solved by gripping the pericardium with at least one outer part end and/or inner part end. A pericardial gripping device comprising at least one inner tube and at least one outer tube, wherein the outer tube has at least one outer diameter and wherein the inner tube has at least one inner diameter, the outer diameter being larger than the inner diameter and the inner tube having at least one inner tube end on at least one inner tube end, and wherein the inner tube end surface has at least one first surface structure and wherein the outer tube has at least one outer tube end surface on at least one outer tube end, and wherein the outer tube end surface has at least one second surface structure, and wherein the first surface structure and the second surface structure are different, solves the object by movably arranging the inner tube in the outer tube.

First advantage of the method: In her master's thesis—Reference 1—, Ms. Sarah Zubke works out the significance of speed for the patient's well-being of an introduction of medical devices using the example of an introducer set. According to her results, devices for inserting guide wires are unsuitable for clinical practice if they do not allow insertion within 55 minutes, preferably 30 minutes, especially 10 minutes. Her results thus make the insertion speed a criterion for evaluating proposed solutions to the state of the art. A reversal of Ms Zubke's results thus allows the conclusion to be drawn that a procedure and a device gain in value if they allow the introduction of medical devices into the pericardium in a short period of time—the shorter the better.

By way of the disclosed method, a medical device may be quickly introduced into the pericardium. Its uncomplicated method steps and the method step of grasping the pericardium both contribute to this speed.

By penetrating the human body with at least one end of the device until it touches the pericardium, the heart or a layer on the heart, all three of them may be quickly located. penetration becomes particularly rapid because it is even easier for a person undergoing treatment if the device is rigid so that the end of the device may be inserted through the human body.

Among others, the following definition may be made as infiltration time: The time between the moment when a human body is opened and the moment when a temporary cardiac assistance system is put into an intended operation.

The second advantage of the method: Gripping the pericardium, the heart or a layer lying on top of the pericardium with at least one external end may be done quickly.

Third method advantage: As it is characterized by gripping pericardium, it has the advantage of being able to distance gripped pericardium from the heart. The spacing opens a space between the pericardium and the heart into which a puncture or cutting tool may enter after penetrating the pericardium without the penetration directly endangering the heart by the penetration of the tool, because the tool penetrates indirectly into the space. Vice versa, the fourth advantage of the method is therefore the increase in treatment safety.

Also, a device for grasping pericardium comprising at least one inner tube and at least one outer tube, wherein the outer tube has at least one outer diameter and wherein the inner tube has at least one inner diameter, the outer diameter being larger than the inner diameter and the inner tube having at least one inner tube end surface on at least one inner tube end, and wherein the inner tube end surface has at least one first surface structure and wherein the outer tube has at least one outer tube end surface on at least one outer tube end, and wherein the outer tube end surface has at least one second surface structure, and the first surface structure e and the second surface structure are different, solves the object by movably arranging the inner tube in the outer tube.

First device advantage: The device follows the principle of "assembled tubes, or assembled hoses", one of whose deductive is their small volume. The existence of a small volume device according to the disclosure may lead a treating person to a behavior of minimally invasive opening of the human body. Leading the treating person to this patient-friendly behavior is therefore the first advantage of the device. In addition to a number of known secondary advantages, for example rapid wound healing of a minimally invasive procedure, its primary advantage is its rapid execution.

Second advantage of the device: Surprisingly, the device further protects a patient because it allows a grip in the first attempt. This advantage is based on two premises. The first is that it may be used to grasp all kinds of human tissue. The second is that multiple grasping of human tissue is stressful for a patient, i.e. one-time grasping is gentle on human tissue. If a type of tissue has been grasped with the device and a single grasp is generally gentler, the treating person does not have to grasp a certain type of tissue.

Third advantage of the device: When using the device, the displacement of fat is of great benefit.

In a preferred embodiment, an outer part is twisted against an inner part to grip the pericardium. The twisting is carried out by the handling of a treating person, i.e. in a first consequence it is mechanical. In a second consequence, it is therefore a grasping, and is thus a mechanical grasping in the overall consequence. This phenomenologically allows a feedback to the treating person. The advantage of mechanical grasping is its inherent feedback of the gras during grasping and the gripping in the grip. This advantage, the tactile feedback, promotes safe and fast work by the treating person.

In a preferred embodiment, at least one outer tube is twisted against at least one inner tube to grip the pericardium with the outer part. Due to this type of gripping, the gripping gains in positional or positional constancy. A requirement of this type of gripping is fulfilled when an inner part positions the device opposite the pericardium. Then, assemblies of the outer part—which is positively guided by the inner part—may be twisted several times against each other, because the constancy of the position of the device is not caused by the outer part, but by the inner part.

In a preferred embodiment, a first outer part end surface is twisted against a second outer part end surface for gripping the pericardium, i.e. a first end face is twisted against a second end face.

When surfaces rub against each other, they are engaged. This engagement is the result of a—microscopic—entanglement of their surface structures. The strength of the engagement, the holding force of the grip is proportional to the catching. Due to the upper set: the more gradual the twist, the stronger the snagging, and the lower set: the stronger the snagging, the stronger the holding power, closes the figure in ponens mode: the more gradual the twist, the stronger the holding power. The advantage of twisting outer part end surfaces is an increase in holding power. This increase is further enhanced when the outer part end surfaces are twisted against each other.

If surface structures are introduced into the outer part end surfaces, the holding force is further increased. It is advantageous if grooves, scores, flutes or cables are incorporated into the surface. Their structure may be periodic, fanned or overlapping.

Because the outer part end surfaces are located at one end of the outer part, the geometry of the outer part end surfaces may be changed easily and advantageously. This change may promote an increase in the holding force if a position angle between the surface vector of an outer part end surface and the outer part is increased or decreased.

In a preferred embodiment, the gripped pericardium is mechanically lifted from the heart by the device.

Lifting spaces apart the heart from the pericardium. This safety distance secures the heart against intentional or unintentional penetration of a puncture or cutting tool by a treating person.

In a preferred embodiment, the inner part is removed from the device.

Removal opens a passage in the outer part, providing access to the pericardium. The advantage of this access is that tools may be passed through it to the pericardium. If these tools are puncture or cutting tools, the pericardium may be manipulated to open it.

The opening may be shaped as a dot, a slot, or a star, made by cutting or punching.

The opening advantageously allows dry punctuating by mechanical lift-off.

In a particularly advantageous embodiment, a punching tube is fed to the pericardium. One end of the tube is sharpened in a favourable continuation to the blade, so that a round section may be punched from the pericardium into the pericardium. Punching has the advantage of forming a clean cutting edge. This prevents further tearing of the pericardium.

If a tool is inserted through the device into the heart during the procedure, different measures may be taken depending on the tool.

If a signal is generated by the device during the procedure for those cases in which it touches the pericardium or the heart, its signal generation positively contributes to the speed of the procedure. A signal to an attending person guiding the device is suitable to induce the attending person to change the action, to move the outer part over the inner part. The signal or a signal display may be automatic, or semi-automatic, optical, acoustic or haptic. If different signals, e.g. an acoustic signal, such as a beeping sound, and a haptic signal, such as a shaking or pressing, are combined, the signal effect is increased so that the procedure may be carried out even faster and more safely. Combining signals increases the redundancy. Depending on the signal, an automatic stop or automatic engagement of a brake may also be provided. This has the advantage that a process point may be displayed from which increased care must be taken. It is of particular advantage if an automatic stop is triggered 1 mm before the pericardium. The safety of the method is further increased if at least one camera that is able to view the pericardium is part of the method. A mechanical brake, e.g. a detent or spring brake, or an electronic brake, e.g. an electromagnetic brake, further increases safety.

If the pericardium is gripped by at least one tooth on the device during the method, it may be twisted behind the teeth by slightly swiveling the device or its parts.

In a preferred embodiment of the device, the inner tube is rotatably mounted in the outer tube.

By turning or partial turning, i.e. by pivoting the inner tube in relation to the outer tube, its end faces are swiveled against each other. This pivoting results in the advantageous gripping of the pericardium, if it is arranged in front of or against the end faces.

In a preferred embodiment of the device, at least one inner part is present, whereby the inner part is movably arranged in the inner tube.

If the inner part, e.g. a probe or a cannula, may be pushed through the inner tube, the inner part may be gently advanced up to the pericardium, where it may be used according to its function, e.g. sensing, gripping, sealing or closing. The advantage of a movable arrangement is that it allows for a tool change. In the example of closing, stapler, suture and heat or laser tools may be used one after the other to close the opened pericardium.

In a preferred embodiment of the device, at least one sensor probe is present in at least one through hole of the inner part.

It is advantageous if this probe provides a haptic signal in the moment the probe reaches the pericardium.

In a preferred embodiment of the device, at least one spring element is arranged between a surface of the inner part and a surface of the sensor probe head.

This has the advantage of buffering contact between the probe head and the pericardium.

If at least one tube is flexible, especially a hose, the entire device is flexible. This simplifies handling of the device.

BRIEF DESCRIPTION OF THE DRAWINGS

FIG. 1 shows a device for grasping the pericardium of a patient in a schematic sectional view.

FIG. 1a shows a device for grasping the pericardium of a patient in a schematic sectional view from the side.

FIG. 1b shows an outer part of the device in a schematic sectional view from the side.

FIG. 1c shows an inner part of the device in a schematic sectional view from the side.

FIG. 1d is a detailed view of a backup.

FIG. 1e is a view along the section E0-E0.

FIG. 2 shows different views of an outer part end of the device for grasping the pericardium of a patient.

FIG. 2a is a detailed view of an outer part end in a schematic sectional view from the side.

FIG. 2b is a sectional view of an outer part end from right to left.

FIG. 2c is a sectional view of an outer part end from left to right.

FIG. 3 shows a first preferred continuation of the device for grasping the pericardium of a patient as a so-called "serrated gripper".

FIG. 3a is a schematic view of a first alternative of the "serrated gripper" from the side.

FIG. 3b is a schematic view of a second alternative of the "serrated gripper" from the side in schematic section.

FIG. 3c is a schematic view of a further configuration of the "serrated gripper" from the front.

FIG. 5 shows a schematic flow chart of a procedure for grasping the pericardium of a patient.

FIG. 6 is a schematic representation of the positions of the device for grasping the pericardium of a patient in its use.

FIG. 6a shows a position of the device in the human body.

FIG. 6b shows a position of the device for grasping the pericardium of a patient in which one of its ends touches the pericardium.

FIG. 6c shows a position of the device for grasping the pericardium of a patient in which one of its outer part ends touches it.

FIG. 6d shows a layer of the device for grasping the pericardium of a patient, whereby the pericardium is gripped with an outer part end.

FIG. 8a is a detailed view of a device for grasping the pericardium of a patient in a gas permeable position of use.

FIG. 8b shows a detailed view of a device for grasping the pericardium of a patient in a gas-tight position of use.

FIG. 9a is a detailed view of a device for grasping the pericardium of a patient in a gas permeable position of use.

FIG. 9b is a detailed view of a device for grasping the pericardium of a patient in a gas-tight position of use.

FIG. 10 is a schematic representation of layers of a device for the insertion of an implant.

FIG. 11 is a schematic diagram of the positions of an implant.

FIG. 11a shows a layer of an implant within the device for grasping the pericardium of a patient.

FIG. 11b shows a position of an implant within the device for grasping the pericardium of a patient.

FIG. 11c shows a layer of an implant.

DETAILED DESCRIPTION

Figure 4:
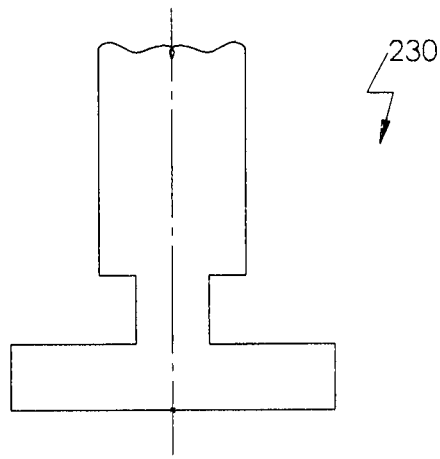
FIG. 4 shows a second preferred continuation of the device as a so-called "groove gripper".

FIG. 1 shows a schematic sectional view of a device for grasping the pericardium of a patient.

Phenomenologically, the device teaches how to grip human tissue (not shown) by stretching a section of tissue (not shown). It teaches tensioning as the result of a conditional displacement of at least two different tissue subsections (not shown). The different tissue subsections (not shown) are to be moved in different directions in order to tension them together. The more the displacement, the more the tension, the stronger the grip of the device. Because the application of a force precedes each displacement of a tissue sub-section (not shown), the gauge of the device may also be understood as a phenomenon that describes the application of at least two forces in different directions to a defined surface element.

The phenomenon is sensory determined as a grasping. Grasping is a tensioning of tissue as a result of its multiaxial displacement. Its sub-phenomenon, uniaxial displacement of tissue sections by at least two rotations, is referred to as "ring gripping". Ring gripping may involve fixing and pulling, holding and retracting, or temporary joining and forced guidance.

In FIG. 1a, the device 10 is shown in a preferred embodiment as a "ring gripper".

In a preferred embodiment, the "ring gripper" comprises at least one outer part 40 in which an inner part 90 is guided. The outer part 40 in turn comprises an outer tube 50 and an inner tube 70. Both the outer and the inner tubes 50, 70 are circular in cross-section.

In the preferred embodiment, the tube 50 and the inner tube 70 may also be hoses (not shown) or parts of hoses (not shown), so that an inner hose (not shown) is guided in an outer hose (not shown). In the embodiment of a hose, the freedom of movement for the patient is increased. As a shaft, the hoses may have a flexible shaft.

In its first sub-embodiment the outer tube 50 is manufactured as outer knurling wheel 60, the inner tube 70 as inner knurling wheel 80. The phenomenon of ring gripping may be determined in this sub-embodiment because it links at least two partial functionalities: contacting the outer part 40 with the pericardium 34; ring gripping the contacted pericardium 34. A (partial) rotational twisting of the outer knurling wheel 60 against the inner knurling wheel tensions tissue sections (not shown) of the pericardium 34 at the site of contact above the heart 31—the direction of rotation of the outer knurling wheel (not shown) counters the direction of rotation of the inner knurling wheel (not shown).

In its first alternative embodiment, the outer part has an outer guide (not shown) instead of an outer tube, for example an outer linear guide (not shown). Preferred linear guides include profile rails with a U, V or T profile.

In its second alternative embodiment, the outer part includes both an outer tube and an inner tube or a combination of both in the form of a polygonal tube (not shown). A polygon tube is polygonal in its cross-sectional profile. Preferred cross-sectional profiles for polygon tubes are square, pentagonal, hexagonal or octagonal profiles.

In the preferred embodiment, all assemblies and components, especially the outer knurling wheel as well as the inner knurling wheel, are made of aluminum or titanium. Preferably they are all milled or turned from an aluminum or titanium block. In further alternatives, they may all be made of steel or other biocompatible materials. Biocompatible materials according to ISO 10993, —besides steel especially also plastic—are preferred.

In the preferred embodiment, an inner tube 70 is mounted in the outer tube 50. The outer diameter of the outer tube (cf. FIG. 1b) corresponds to the outer diameter of the inner tube (cf. FIG. 1b), so that the outer surface of the inner tube 70 together with an inner surface of the outer tube 50 guides the inner tube in the outer tube. In a further embodiment, partial surfaces lead the tubes to each other. They may be at least one mantle surface section (not shown) of the inner tube 70 or at least one inner surface section (not shown) of the outer tube 50. In a further embodiment, the inner tube 70 is biaxially guided in the outer tube 50. The axes lie in the longitudinal and circumferential direction of the ring gripper 13, so that the inner tube 70 may be manipulated in two degrees of freedom relative to the outer tube 50.

In the preferred embodiment, an inner part 90 is loosely and unidirectionally mounted in the outer part 40. The inner part 90 is thus movable in the outer part 40 in axial direction 15. The guide forces the inner part 90 in the outer part 40 to move in axial direction 15.

The preferred embodiment in FIG. 1a shows the principle of "assembled tubes". The ring gripper 13 is formed by inserting its inner part 90 into the outer part 40. The outer part is formed by inserting the inner tube 70 into the outer tube 50. Thus, the phrase "all components are plugged together" applies. Because inner part 90 and outer part 40 are also a type of tubes, the phrase "all components are tubes" applies. Thus, in the mode ponens, the phrase "all tubes are plugged together" applies. This principle may also be described as "tubes plugged together".

In its second sub-embodiment the inner part 90 is formed as pin 100. At least one through hole 102 is made in pin 100. It is preferably drilled over its entire pin length 109. A pin hole 106 is countersunk into the pin tip 105. The pin 100 has an outer pin diameter 101.

In the preferred embodiment, the inner part 90 includes a probe. This is divided into a probe shaft (see FIG. 1c) and a probe head (see FIG. 1c). The probe shaft (see FIG. 1c) is inserted in the through hole (see FIG. 1c) of the inner part 90. It is secured against slipping out in the axial direction 15 towards the tip of the device 13 by means of a securing device 130 on the side of the ring gripper 13 opposite the tip of the inner part.

FIG. 1b shows a schematic sectional view of an outer part 40 of the device from the side.

In the preferred embodiment, the inner tube 70 is inserted into the outer tube 50, an inner knurling wheel 60 is inserted into an outer knurling wheel 80. The inner tube 70 has at least three inner tube collars 76:—from right to left—a first inner tube collar 76 at the proximal end of the device 12; a second inner tube collar 76 at a distance from the first; a third inner tube collar 76 at a distance from the second inner tube collar 76. The first inner tube collar 76 is a handle, the second inner tube collar 76 ensures that the inner tube 70 does not slip out of the outer tube 50 in an axial direction 15 towards the tip of the device 13, the third inner tube collar 76 may secure the inner tube 70 against complete axial movement. For this purpose, the third inner tube collar 76 is guided in a groove of the outer tube.

Also, in the outer tube 50 at least a first outer tube collar 56 is manufactured, especially turned. This outer tube collar 56 also forms a handle.

In all embodiments, all handles may be knurled so that a treating person may hold them firmly. Furthermore, in all embodiments the outer diameter 51 of the outer tube of the handle of the outer tube 50 may be larger than the outer diameter of the inner tube 71 of the inner handle. Furthermore, in all embodiments, the outer diameter as well as the inner diameter may vary along the length of the device.

The inner diameter 72 of the inner tube is manufactured in such a way that a variety of tools may be passed through it.

FIG. 1c shows an inner part 90 of the device 10 in a schematic sectional view from the side.

The inner part 90 in the preferred embodiment comprises at least four components: a pin 100, a probe 110, a spring element 120 and a safety device 130.

In the preferred embodiment, the pin 100 is manufactured tiered. The tip 105 of the pin, which points in the direction of the pericardium (not shown), is conical. From the tip 105 of the pin, the outer pin diameter 101 increases towards the knob 108 of the pin. At the outermost end of the tip 105 of the pin, the pin diameter 101 is thus the smallest.

A pin lock is countersunk into the pin tip 105. Its pin hole diameter 107 is larger than the through hole diameter 103. Pin 100 has a pin collar 104 at one end.

The probe 110 comprises a probe shaft 111 and a probe head 112.

In the preferred embodiment, the inner part 90 is fitted in a first step by arranging the spring element 120 over the probe shaft 112, and then in the second step by inserting the probe shaft with spring element 120 through the through hole of the pin 100, so that finally in the third step the probe 110 may be secured against falling out or slipping out of the pin 100 by means of the safety device 130 (see FIG. 1d).

FIG. 1d shows a detailed view of a safety device. The safety device is located at the free end of the pin knob 108. The free end of the pin knob 108 is ventral in a preferred position for use. In an alternative use position it is lateral. Both positions of the free end of the pin knob 108 mark its position according to the main anatomical directions away from the body. The safety device 130 prevents the probe from slipping out of the pin in the dorsal direction, in which a retaining ring 132 fits, preferably press fits, into a retaining groove 131.

In an alternative embodiment, a locking cotter pin (not shown) may also be inserted into a locking bore (not shown), which is drilled transversely to the core of the pin, with positive or frictional locking, e.g. plugged, inserted and bent, fitted, in particular press fitted.

FIG. 1e shows a view along the section E0-E0 from FIG. 1a. In the section the size relations of the handles discussed above become clear.

FIG. 2 shows different views of an outer part end of the device. The outer part end describes a dorsal section of the outer part.

FIG. 2a shows a detailed view of an outer part end 41 in a schematic sectional view from the side.

In the preferred embodiment, its outer part end length 42 is approx. 2 cm long, in further configuration it is 1 cm. In alternative embodiments it is designed according to the elasticity of the pericardium (not shown) or other inner skins (not shown), body layers (not shown), organs or the outer skin. At the dorsal tip of the inner part end there is a volume 16 between the outer tube 50 and the inner tube 70.

In the preferred embodiment, volume 16 is the result of an outer part end shoulder 43. The outer part end shoulder is made out of the outer tube 50 and is manufactured along the inner circumference of the outer part end 41, especially turned or milled.

In an alternative embodiment, a shoulder (not shown) may also be made in the inner tube 70 or shoulders may be made in the outer tube 50 and inner tube 70.

In further configuration of both preferred or alternative embodiments, the shoulders may have different profiles, for example ribbed, rising, curved, jagged or tapered profiles (not shown). Also, a plurality of outer part end shoulders 43 may be made along the inner circumference of the outer part end 41 into the outer tube 50 or the inner tube 70. In particular, the inner tube ends 74, outer part end surface 44 and outer tube end surface 54 may be profiled individually or in combination. Different profiles increase the friction forces along the surfaces and ends.

FIG. 2b shows a detail view of an outer part end as a sectional view from right to left. The detail view shows that the outer part end surface 44 is formed from an outer tube end surface 54 and an inner tube end surface 74.

In a preferred embodiment, this describes a total area. The outer part end surface 44 lies in the dorsal direction, i.e. its surface vector (not shown) points in the direction of the human body (not shown) according to the main anatomical directions, and the same applies to the surface vectors (not shown) of its partial surfaces.

In a further embodiment, both the outer partial end surface 44, i.e. an end face, and its partial surfaces or sections may be profiled. Preferably the profile is manufactured in such a way that a high degree of roughness is achieved. As an example, a high roughness is given if the profile has a roughness value defined in the engineering sciences, wherein the high or low value of the roughness value defines the profile as rough. As one roughness value—among many others—the so-called RA value may be used.

In further embodiment, using the example of the RA values, roughness of the outer tube end face 54 and the inner tube end face 74 differ.

In the use position, a direction of rotation of the outer knurling wheel 61 is opposite to the direction of rotation of the inner knurling wheel 81.

In contrast to FIG. 2b, FIG. 2c shows a detail view of an outer part end as a sectional view from left to right.

An outer tube end surface profile is machined into the outer tube end surface 54, in particular a profile that includes outer tube end surface notches 59a and inner tube end surface notches 79. In the preferred embodiment, the outer tube end surface notches 59a are machined into the outer tube end surface 54 at equal distances (not shown) from each other radially. The inner tube end surface notches are also manufactured radially as inner tube end surface profile 78 into the inner tube end surface at equal distance (not shown) from each other. The main direction of the outer tube end surface notches 59a are substantially opposite, oblique, to the main direction of the inner tube end surface notches 79.

In further detail, the outer tube end surface profile and the inner tube end surface profile 78 differ. The difference is characterized in that at least one first main direction (not shown) of the outer tube surface face profile is opposite to at least one second main direction of the inner tube end surface profile 78.

Alternatively, in further embodiments, the first and second main directions may be substantially opposite. When the first and second principal directions are vectorially interpreted; and when a first sub-vector of the first principal direction vector and a second sub-vector of the second principal direction vector are parallel but opposite, it may be indicated that the first principal direction and the second principal direction are substantially opposite.

In a more detailed configuration, the first and second principal directions may be arbitrarily positioned relative to each other.

If the direction of rotation of the outer knurling wheel 61 is opposite to the direction of rotation of the inner knurling wheel 81, the profiles hook into each other.

FIG. 3 shows a preferred embodiment of the device.

It is called a "serrated gripper". The "serrated gripper" illustrates the phenomenon of mechanical pericardial lifting from the heart by gripping behind the pericardium with tines. This back-gripping may also be called back-prong gripping. Alternative names for the "serrated gripper" are "back-jaw gripper" or "scaled gripper".

A tine usually describes at least one point, hook, barb, slat or scale at the edge. It is usually attached to this edge, an end, at one of its serrated ends. At at least one other end of the tines is sharp-edged, in particular ground and filed. A serrated gripper may also be considered a tooth, for example a saw blade tooth. FIG. 3a shows a schematic view of the first alternative embodiment. It shows a "serrated gripper" as an "outer part serrated gripper".

In a preferred embodiment, the tines 220 are located at the tip of the fixture 13 on the outer part 40, in a further embodiment they are located in the area of the outer part end or in the area of the inner part tip, preferably in the area of the pin tip. In the case that the tines 220 are arranged in the area of the outer part end, an arrangement of at least one tine 220 either in the area of the outer tube end and/or in the area of the inner tube end of the preferred embodiment is also possible.

In the preferred embodiment, tines 220 are provided at the outer tube end 53 for this purpose. In a further embodiment these may be manufactured in one piece with the outer tube 50. In the preferred embodiment, the tines 220 are injection moulded in one shot with the outer tube 50. Alternatively, they may be welded or soldered as individual lamellae to the outer tube end 53.

FIG. 3b shows a schematic view of the first alternative embodiment, with a pin 100 for "jagged gripping".

In the preferred embodiment, the tines 220 are cast in a serrated pocket 222, in the alternative embodiment they are cast on the outer surface of the pin 100, in one piece with the pin 100, preferably at the pin tip 105 in the injection moulding process.

In the preferred embodiment, all tines 220 have the same setting angle 223 to the pin 100, e.g. serration centerline 221 to the pin axis.

FIG. 3c shows a schematic view of the first alternative embodiment from the front. Tines 220 in a scaled form are glued or welded to the tip of the pin as scales. The length of tines 220 (not shown) varies. Therefore, the tines 220 overlap in parts. In the direction of the tips of the tines, in clockwise direction, the tines 220 rotate or swivel in gripping direction 225, whereas they run counter-clockwise in freewheel 224. Swiveling of the serrated gripper involves small, i.e. gradual rotation of the serrated gripper about its axis. Swiveling may take place both in gripping direction 225 and in freewheel direction 224. FIG. 4 shows a schematic view of another alternative embodiment.

This embodiment may be described as "groove gripper" 230.

The "groove gripper" illustrates the phenomenon of a mechanical pericardial stroke by allowing pericardium to flow, be pulled or pressed into a groove made in it so that it may be clamped there.

Figure 4A:
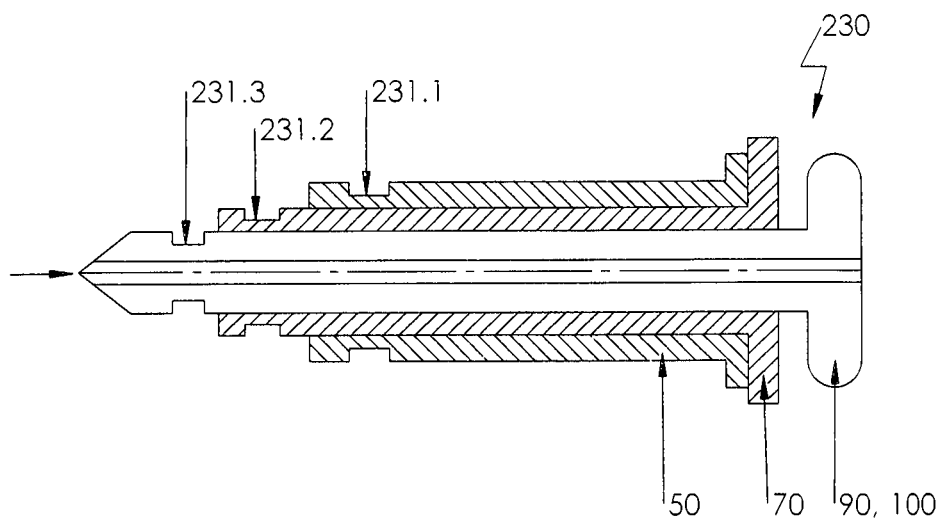
FIG. 4a is a schematic view of the different alternatives of the "groove gripper".

FIG. 4a shows an initial further development of the groove gripper 230.

The first preferred embodiment, the "outer tube slot gripper" is characterized by the fact that at least one slot 231.1 is made in the outer tube 50.

In the second preferred embodiment, the "inner tube slot gripper" is characterised in that at least one slot 231.2 is made in the inner tube 70, in particular in the region of the device tip.

In the third preferred embodiment, the "inner part groove gripper" is characterised in that at least one groove 231.3 is made in the inner part 90, preferably in the pin 100, in particular in the region of the pin tip.

The preferred manufacturing process for the insertion of at least one groove into one of the proposed further developments of the groove gripper is injection moulding. The groove is therefore incorporated, e.g. milled, during the production of the respective further configuration. Alternatively, the groove may be manufactured or reworked in a later work step after completion of the further configuration. Preferably it is milled out for this purpose.

In use, a second type of further configuration is pressed into a tissue section or a tissue subsection, such as the pericardium, until the tissue flows into or behind the groove and is pressed. By swiveling, rotating or partially rotating, in particular turning the groove gripper, the pericardium is then twisted, i.e. swirled, such that the pericardium is frictionally and/or positively mounted in the groove, i.e. fixed, clamped, in the sense of gripped.

FIG. 5 shows a schematic flow chart of a method.

The preferred sequence is shown in FIG. 5 by steps. They are referred to with "S". Thick arrows indicate main steps, thin arrows indicate alternative intermediate steps. Thick ones, like thin ones, run according to plan, but thin ones usually run in loops so as not to overtake thick ones. In contrast to steps, states are represented as boxes. They are marked with "Z">.

In the preferred embodiment in the use position, the surface vectors (not shown) of both the outer tube end surface and the inner tube end surface point in the direction of the pericardium.

In a preferred embodiment step S0, a human body (not shown) is opened. This is done by cutting it open with a scalpel to create a body access opening. The extent of this opening may vary between at least two extreme positions: a minimum possible body access opening, e.g. a puncture, and a maximum possible body access opening, e.g. an open thorax.

Preferably, a treating person will create a subxiphoidal body access. Alternatively, an access may be opened intercostal or apically. The terms mentioned above subxiphoidal, intercostal and apical describe main anatomical directions.

After a body access has been created, it may be used to insert a device, in particular a device according to the disclosure, a ring, serrated or groove gripper (not shown) into the patient (not shown).

In an alternative intermediate step S1b, the body access opening may be secured by the treating person using a suitable tool (not shown).

The device is then used to penetrate the human body in step S1a, in which a treating person advances it. The advancement is characterized by probing, a careful exploration as well as by dilating, creating a space.

In at least one intermediate step S1c, surrounding human tissue (not shown), organs (not shown) or skins (not shown) are displaced or severed in parallel if necessary in order to drive the device further through the human body (not shown). In an alternative intermediate step S1d, the treating person may check which human tissue (not shown) he or she is displacing or severing. The person may also check whether he or she still drives the device towards the pericardium.

As soon as the device touches the pericardium with one of its device ends, the latter generates a signal. In a preferred embodiment, the signal is haptic, i.e. the signal is felt by the treating person. The touch is experienced by noticeably increasing resistance. In a second preferred embodiment, the signal is generated by an electrical signal generator, which may alternatively generate signals acoustically or optically. The signals are recorded by the signal generator so that treatment may be followed.

When condition Z2 is reached, intermediate steps may be initiated by the treating person.

Preferred intermediate steps serve to take a situation picture. An x-ray or ultrasound image or an electrocardiogram (ECG) or a combination of these shall be recorded.

Next, the treating person slides the outer part over the inner part until the tip of the inner part touches the pericardium. If this condition is "Z3", the device is in working position.

If the device is in working position and is a "ring gripper", the pericardium is gripped by twisting the ring gripper. The pericardium is gripped by rotating or partially rotating the outer tube and the inner tube. The rotation or partial rotation of the aforementioned tubes is preferably done in the opposite direction. In a more detailed embodiment, the direction of rotation of the inner knurling wheel is thus opposed to the direction of rotation of the outer knurling wheel.

When the device is in the working position and is configured as a serrated gripper, the pericardium (not shown) is gripped by hooking the pericardium (not shown). The tines (not shown) on the serrated gripper are pressed into the pericardium, preferably slightly depressed, and the serrated gripper is slightly rotated or oscillated so that the pericardium (not shown) or sections of pericardium (not shown) flow behind the tines (not shown), are pressed, pushed or conveyed and become hooked there.

When the device is in working position and configured as a groove gripper, the pericardium is gripped by twisting it. The groove gripper is slightly pressed into the pericardium and/or rotated or oscillated so that the pericardium or its pericardial sections (not shown) flow into the groove, are pressed or conveyed. By increasingly rotating the groove gripper, the pericardium is conveyed further into the groove by being pulled into it. The increase in pericardium compresses it in the groove, resulting in an increase in its frictional and positive locking.

If the treating person has grasped the pericardium in procedure step S3 and is convinced of the grip, then the condition "Z4", the pericardial grip mentioned here, is present.

In further embodiment of the procedure, the inner part may now be removed from the outer part, procedure step S4, so that access to the pericardium as a tunnel, passage, hose or tube through the device, at least one device tunnel, is opened.

A punch tube (not shown) may be inserted through the access in order to punch a puncture into the pericardium. In preferred embodiment, the punch tube is a cannula.

In a further embodiment of the procedure, the treating person may insert an implant into the pericardium through the device tunnel. Preferably the implant is a drainage, a probe or a cushion.

Alternatively, and/or consecutively, the implant may be guided into or out of the pericardium by an implant guide.

FIG. 6 shows a schematic diagram of the positions of the device in use.

FIG. 6a shows a position of the device 10. The device 10 is configured as a ring gripper 20 and inserted into the human body 200 through the body access opening 201. The tip of the device shows a penetration depth 202, i.e. its distance to the body access opening 201. The working depth 203 describes the distance between the pericardium 34 and the body access opening 201. The ring gripper 20 is in working position "Z4" when the tip of the device lies against the pericardium 34, i.e. when it touches it.

FIG. 6b shows a position of the device 10 in the form of ring gripper 20 in pericardial contact, "Z2".

In the working position, the probe head 112 presses against the pericardium 34. The probe pulsates because the pericardium 34 pulsates due to the beating of the heart (not shown), the movement follows consecutively from the strength of the pericardial pulsation and the strength of the spring element 120.

In the preferred embodiment, spring element 120 is a spiral or disc spring, a piece of foam or a piece of rubber.

FIG. 6c shows a working position "Z3" of the device 10 in the form of ring gripper 20.

The outer part 40 touches the pericardium 34 with its outer part end 41, while the inner part 90 is spaced apart from the pericardium 34.

FIG. 6d shows a device 10 with gripped pericardium, pericardial grip "Z4".

Figure 6E:
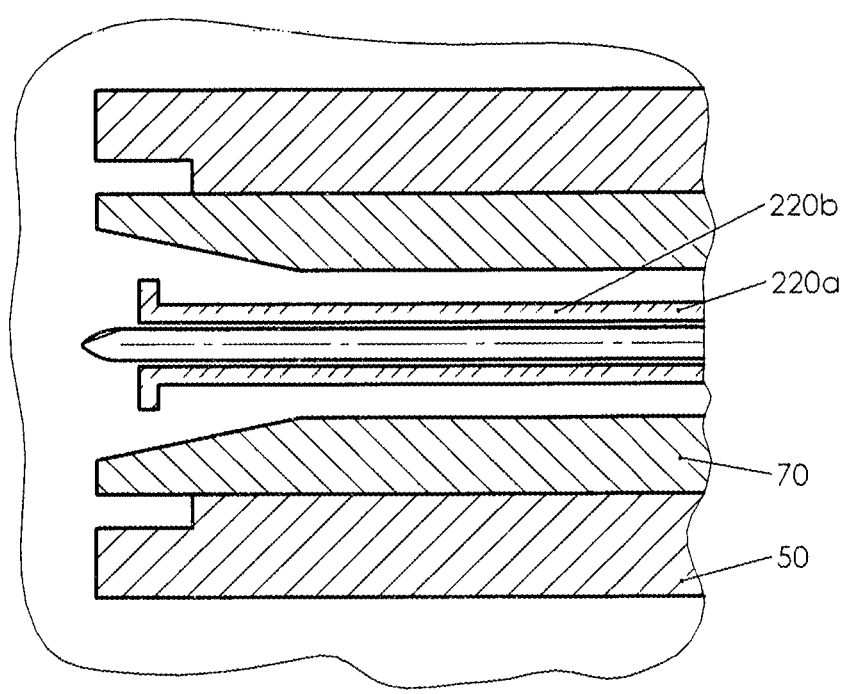
FIG. 6e shows an alternative embodiment of a device according for grasping the pericardium of a patient as a serrated gripper.

FIG. 6e shows an alternative embodiment of a device with a serrated gripper 220a in an insertion position. The serrated gripper 220a is guided by an inner tube 70 and an outer tube 50 at its serrated gripping shaft 220b.

Figure 6F:
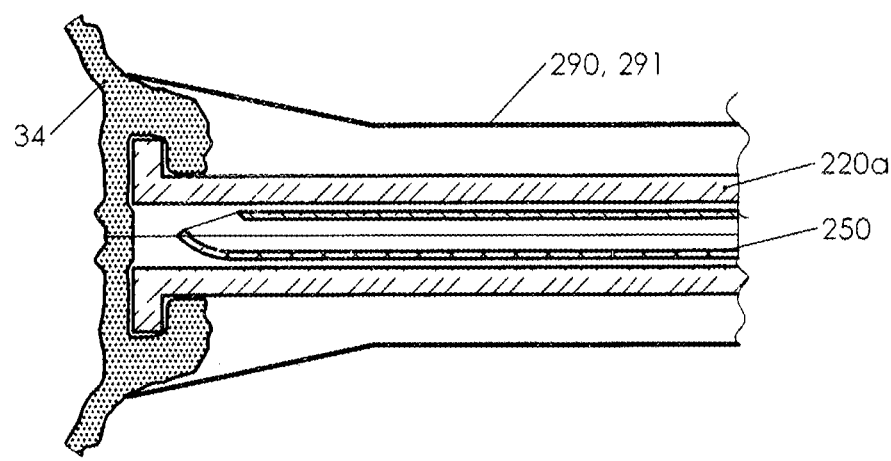
FIG. 6f shows an alternative embodiment of a device for grasping the pericardium of a patient as a serrated gripper in an insertion position.

FIG. 6f shows another preferred variant. The serrated gripper 220a is only guided by a support structure 290. This may be an inner tube (not shown), a hose (not shown) or a so-called soft tissue retractor 291. If the support structure 290 is a soft tissue retractor 291, it may be positioned on at least one section of pericardium 34. In preferred advanced configuration, the soft tissue retractor 291 has a funnel at its apical end. The serrated gripper 220a may be advanced through it until it touches the pericardium 34. By slightly swiveling the pericardium 34, a blind hole is cut into it by the tines 220 (see FIG. 3), into which the serrated gripper 220 may be plugged in. If this grips the pericardium 34, a puncture needle 250 may be advanced to open the pericardium 34. In FIG. 6f, the serrated gripper 220a is in a gripping position, i.e. the serrated gripper 220a and the pericardium 34 form at least one temporary hold. In the preferred embodiment, this results from the flowing of pericardium 34 or pericardium parts (see FIG. 3c) around the tines (see FIG. 3c) or from mechanical penetration of the tines 220 into the pericardium 34.

Figure 6G:
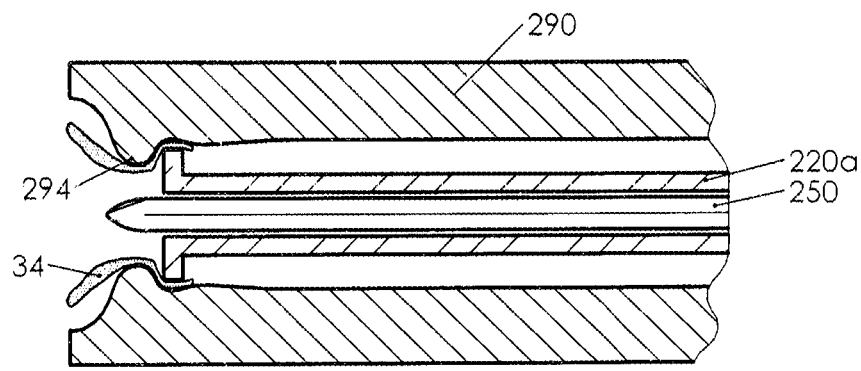
FIG. 6g shows an alternative embodiment of a device for grasping the pericardium of a patient as a serrated gripper in one grip position.

FIG. 6g shows another preferred embodiment. This has at least one locking shoulder 294. In use, the serrated gripper 220a is advanced through a support structure 290 and pericardium 34 is gripped by tines (not shown, see FIG. 3). The gripped pericardium 34 is taken along and pulled behind the locking shoulder 294 to clamp it. Phenomenologically, the tines (not shown) thus form drivers. Once the pericardium 34 is clamped, a puncture needle 250 is advanced to open the pericardium 34. The support structure 290 is made of an elastic material so that it may bend open when the pericardium 34 is pulled behind the locking shoulder 294 by the serrated gripper 220a.

Regardless of the type of embodiment, the serrated gripper has circumferential tines (see FIG. 3) at its apical end, i.e. at least two tines are arranged along the circumference of the serrated gripper. These are milled from solid titanium or aluminium. Preferably, the serrated gripper is made in one piece for this purpose. Alternatively, the serrated gripper may also be made in two pieces. The apical end is punched from a blank, resulting in a circular saw blade or a cutter (see FIG. 3c). This is alternatively glued, clamped, pressed or welded to at least one section of the serrated gripper shaft.

In a preferred embodiment, the serrated gripper runs freely against the shape of the tines. This direction forms the so-called freewheel. In the opposite direction, i.e. clockwise, FIG. 3c shows the serrated gripper running in the gripping direction. During the movement in the circumferential direction, the gripping tool, which is provided with tines on the circumference, may dig into the wall of the blind hole of the pericardium with the tines and slide along the wall of the pericardium in the other circumferential direction.

Figure 7:
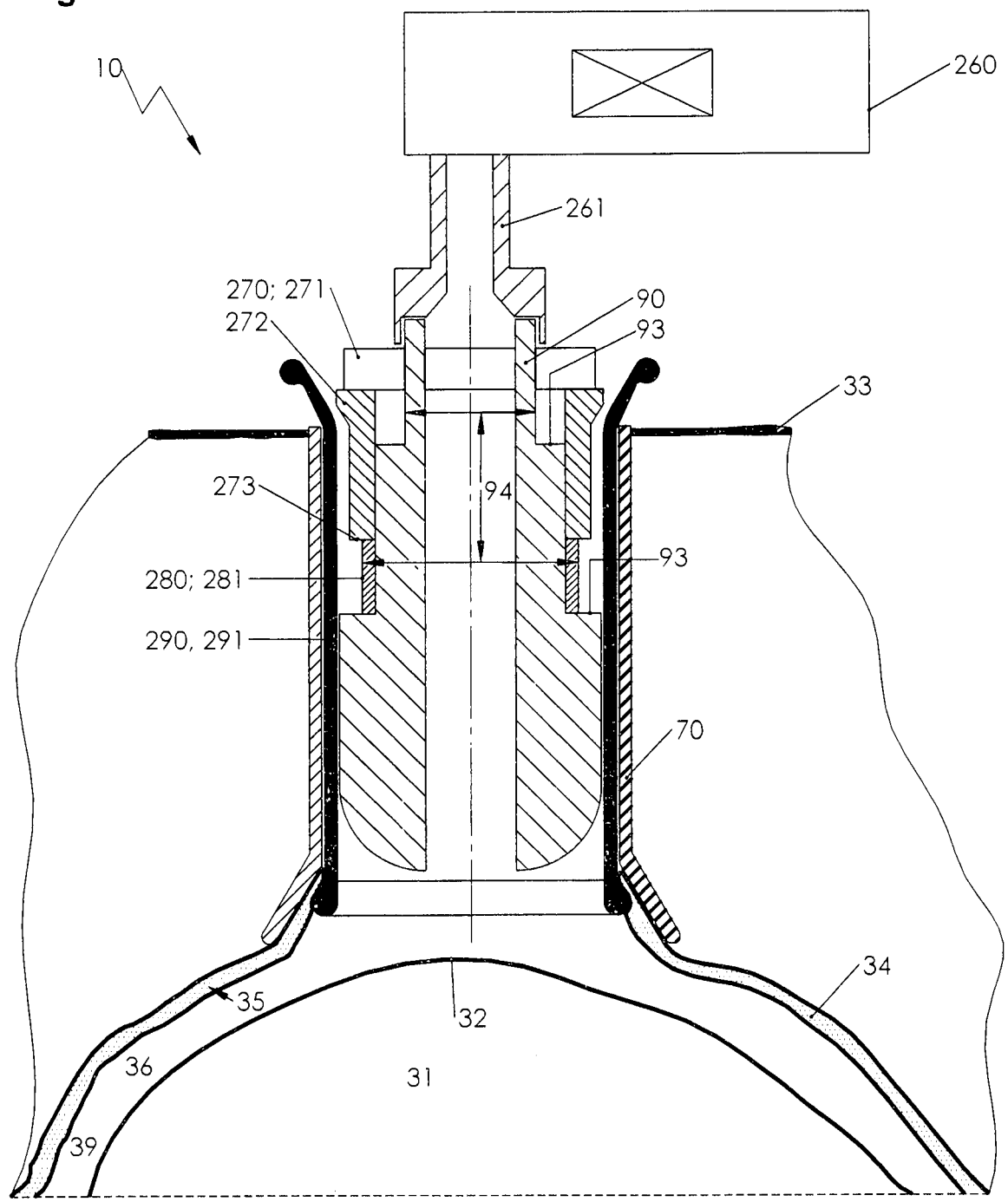
FIG. 7 shows a device for grasping the pericardium of a patient in a position of use with seals.

FIG. 7 shows a device 10 in a position of use with sealings 280. Those sealings seal the open pericardium 34 against the device 10 so that free fluid flow, e.g. a gas flow (not shown) into or out of the pericardium 34 is prevented.

The aforementioned embodiment may also be used independently of other embodiments.

The pericardium 34 is under pressure within its physiological limits (not shown). This pressure, the internal pressure of the pericardium 36, is reduced compared to the ambient pressure (not shown) in the interval of approx. −15 mmHG to 0 mmHG. Within physiological parameters, the internal pericardial pressure 36 is therefore a negative pressure. The negative pressure fills an internal volume 39 between the heart 31 and the inner side of the pericardium 35.

The problem is that opening the pericardium 34 may result in a serious loss of pumping capacity of the heart 31.

If the pericardium 34 is opened without sealing, the ambient pressure and the internal pressure 36 of the pericardial sac equalize, the pericardium 34 loses its internal compression, so that the heart 31 is no longer held in a functionally supportive form. The plane of the heart valves (not shown) and the tip of the heart are connected by tissue. As long as the tip of the heart 32 is sucked into the pericardium 34 by the negative internal pressure of the pericardium 36, i.e. a negative pressure, the pericardium 34 keeps the heart 31 in its typical contour. Because the apex 32 is held, the plane of the heart valves moves in relation to the apex. Without negative pressure, however, the apex 32 is loosely supported in the pericardium 34, so that it moves in relation to the plane of the heart valves. This reduces the functionality of the heart valves (not shown), including their stroke, which results in a decrease of the pumping capacity of the heart 31. The loss of power assistance corresponds to a loss of pumping power of the heart 31 of more than 20%.

The problem is solved by keeping the internal pressure of the pericardium 36 under pressure before, during and after treatment, i.e. below ambient pressure. Phenomenologically, the device 10 is therefore sealed against an increase in the internal pressure of the pericardium 36 to the ambient pressure. It is monitored and controlled by at least one vacuum pump 260. In the position of use, the embodiment variant in FIG. 8 comprises an inner tube 70 through which a support structure 290 is passed.

In a preferred embodiment, the support structure 290 is a so-called soft-tissue retractor 291, which acts advantageously as a moisture barrier and seals against fluid loss.

An inner part 90 is movably guided by the support structure 290. Its degree of freedom may be predetermined by different tolerances in different embodiments. In the case of a standard tight embodiment, the inner part 90 is fitted against the support structure 290 at the transition, so that both friction partners seal against each other due to minimal friction. Sliding gel is used as an insertion aid, which is applied to the inner part 90 before it is guided through the soft-tissue retractor 291.

The inner part 90 is manufactured with steps, preferably inner part collars 93 are extracted of the solid material, e.g: titanium, aluminum or steel alloys, e.g. milled or turned and inserted through the skin 37. The inner section collars 93, (steps) vary in their inner section diameter 94, they increase from top to bottom in FIG. 8, i.e. in the apical direction. In a preferred embodiment, a first inner section collar diameter 94 (step diameter) is smaller than a second, apically twisted inner section collar diameter 94. An elastic body, a sealing 280 is mounted on the second inner section collar diameter 94. In advantageous configuration the sealing 280 is a stuffing box 281, which is made of an elastomer such as rubber or silicone, for example, and is pushed with clearance onto the second inner part collar diameter 94. An additional spacer 272 is guided over the second inner part collar 93. This spacer is loosely mounted axially along the length of the inner part. At its apical end, the apical spacer end 273, it touches the stuffing box 280 in the position of use shown. The actuating force of a mechanical mechanism 270, in a preferred embodiment the tightening force of a nut 271, is transmitted to the spacer 272 because the spacer 272 is loosely mounted, so that the stuffing box 281 is compressed and deforms according to its elastic behaviour. Its expansion will decrease axially and increase radially until it first contacts and then presses against the inside of the soft tissue retractor 291. The introduction of a tightening force thus results in a sealing between the inner part 90 and the soft tissue retractor 291 by pressing in a shaped body.

A vacuum pump 260 is attached by a flange 261 at the ventral end of the inner part 90, i.e. in FIG. 7 at the upper end of the picture. In a preferred embodiment, this pump maintains a pressure below ambient pressure before, during and after the insertion of the device 10. Advantageously, a control of the negative pressure may be used to support heart contraction. This support may include, in a preferred configuration, either static or dynamic pressure changes or both of the above-mentioned pressure changes.

The object is also solved by providing an airlock (not shown). For this purpose, an airlock chamber (not shown) may be placed on the inner part 90 or flanged on as soon as pericardium 34 is open.

As soon as the inner part 90 has been hooked to the pericardium, an opening tool, e.g. a serrated gripper (not shown) may be inserted into the inner part 90 as soon as all chambers (not shown) of the airlock have been brought to the same negative pressure.

After reaching this negative pressure a slide (not shown) between at least two chambers (not shown) may be opened and a used tool may be pulled out of the chamber into the lock chamber. Then the slide valve between the two chambers is brought back into the closed position. Afterwards the lock chamber may be opened and the used tool may be exchanged for another one. After closing the lock chamber, the vacuum is generated again in the airlock chamber so that the slide (not shown) may be opened again and the new tool or the implant (not shown) may be brought into position through the construction. It is advantageous that a tool change may be repeated as often as required.

The opening tool will then be actuated from outside the airlock in a preferred embodiment. For this purpose, small hydraulically actuated lifting cylinders and cylinders for a rotary movement are available in the technology, which may also be accommodated in the tubes. Alternatively, these hydraulic cylinders may be integrated into the pipe construction. After a pericardial opening 34a, e.g. in view of a treatment, the problem arises to close the pericardial opening 34 again. This object is solved by the device 10, in that the vacuum pump 260 creates a vacuum in the pericardium 34, which is suitable for creating a certain negative pressure there, so that the heart 31 is pulled into a physiological shape. By drawing the negative pressure, the device thus consecutively solves the object of restoring a functionality of the heart valve plane before the pericardium 34 is closed. In a preferred embodiment, the pericardial opening 34a is closed by laser, suturing, gluing or stapling.

Figure 8:
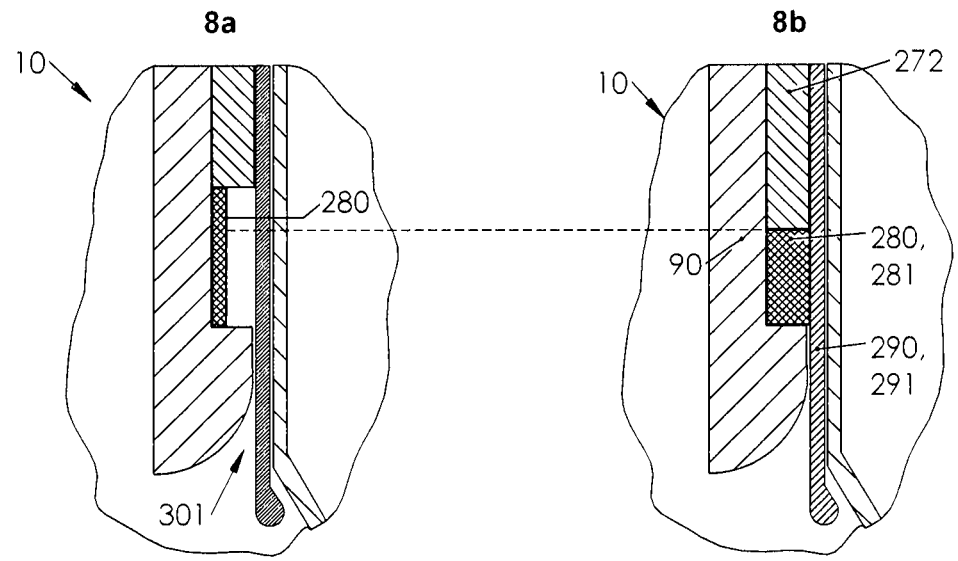
FIG. 8 is a detailed view of a device for grasping the pericardium of a patient.

FIG. 8 shows a detailed view of a device in two different states: closed and open or sealed and gas permeable, respectively.

FIG. 8a shows a detailed view of a device 10 in a gas permeable position of use. The moulded body, the stuffing box 280 is free of compression forces, so that at least one gap 301 results.

FIG. 8b shows a detailed view of a device 10 in a gas-tight position for use. The sealing 280, i.e. the stuffing box 281, rests on the soft tissue retractor 291, a support structure 290, so that a free gas flow (not shown) is prevented by gaps (cf. FIG. 8a); the inner part 90 is sealed against the soft tissue retractor 291. For sealing, the spacer 272 presses the stuffing box 281 together.

Figure 9:
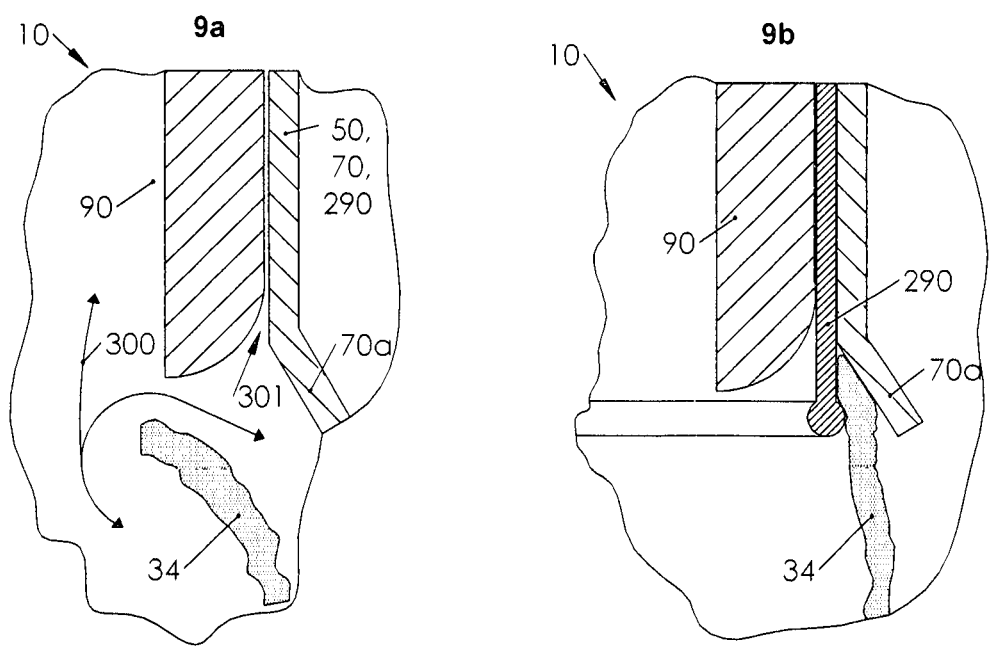
FIG. 9 is a detailed view of a device for grasping the pericardium of a patient.

FIG. 9 shows a detailed view of a device in two different states: gas permeable and gas tight.

FIG. 9a shows a detailed view of a device 10 in a gas permeable position of use. The pericardium 34 is severed, resulting in a gas flow 300 into or out of the pericardium 34. FIG. 9a shows three gas flows 300, one flowing in a first path through at least one first inner part bore into the pericardium 34, in a second path between at least one outer surface of the inner part 90 and a support structure 290, a tube 70 or 50, in a third path between the outer surface of the inner part 90 and at least one open end, i.e. a cone 70a. FIG. 9b shows a detailed view of a device 10 in a gas-tight position of use. The pericardium 34 is clamped between the support structure 290, between a soft tissue retractor and a cone 70a and is thus sealed.

FIG. 10 shows a schematic diagram of positions of a device for the insertion of an implant (not shown).

The aforementioned embodiment may also be used independently of other embodiments.

Figure 10A:
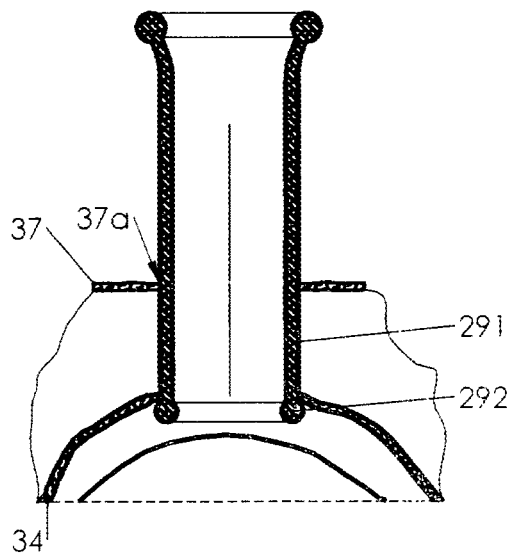
FIG. 10a is a schematic view of an open treatment site.

FIG. 10a schematically shows an opening position at a treatment site. A skin section 37 or skin 37 is severed so that an insertion opening 37a is opened. It is placed e.g. by a scalpel incision. A soft tissue retractor 291 may then be advanced through the insertion opening 37a.

In a preferred method, its feed stops as soon as it rests on the pericardium 34. The contact may be felt, palpated or optically checked manually or mechanically. When the soft tissue retractor 291 is in contact, a cutting or pushing instrument may be guided through it and advanced until the pericardium 34 is reached and severed. Alternatively, the pericardium 34 may be opened with at least one cannula (not shown), special tools (not shown), e.g. ring, groove or serrated gripper, a needle (not shown) or a scalpel (not shown). One end of the soft tissue retractor 291 is advanced through the opened pericardium 34 until its apical clamping ring 292 is clamped behind the pericardial opening.

Figure 10B:
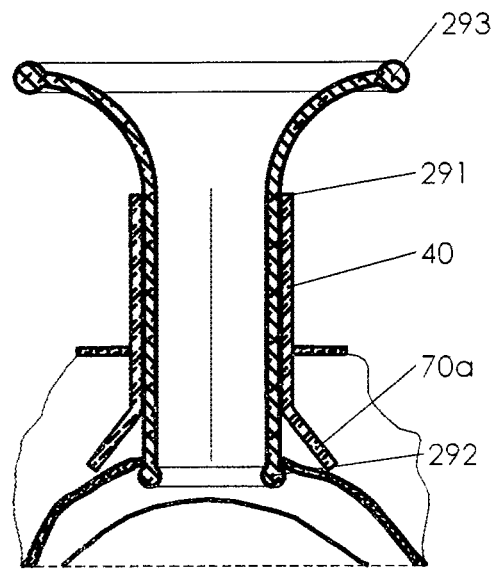
FIG. 10b is a schematic view of an open treatment site with a soft tissue retractor.
Figure 10C:
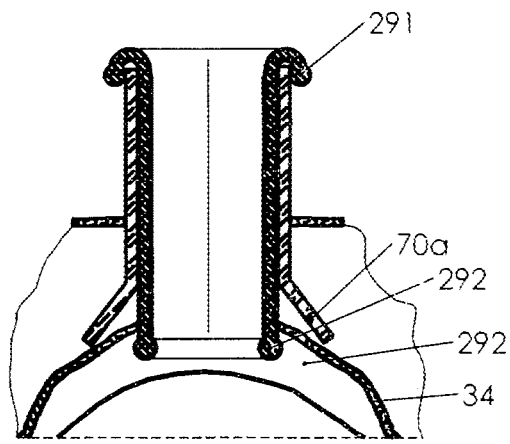
FIG. 10c shows a tensioning of a soft tissue retractor.

FIG. 10b schematically shows an opened treatment site with an inserted soft tissue retractor 291. An apical tension ring 292, an anterior tension ring 293 or both of the soft tissue retractor 291 are folded, compressed, crumpled manually or mechanically until he or she may be passed through at least one outer part 40 or an inner tube (not shown) or an outer tube (not shown) or a plug connection of inner and outer tube (see FIG. 6e). In the preferred embodiment, the outdoor part is a so-called sleeve tension funnel. If the soft tissue retractor 291 is guided through a sleeve tension funnel, the sleeve tension funnel is advanced towards the pericardium until it touches the entrance of the funnel, i.e. a cone 70a. FIG. 10c shows a clamping of a soft tissue retractor 291 to clamp pericardium 34 between an inner side of a cone 70a and an apical clamping ring 292 of a soft tissue retractor 291. For this purpose, the upper end of the soft tissue retractor 291 is pulled at the ventral clamping ring 293, in the picture the upper end of the soft tissue retractor 291. At least parts or sections of the apical clamping ring 292 take pericardium 34 with them until it clamps in cone 70a.

Figure 10D:
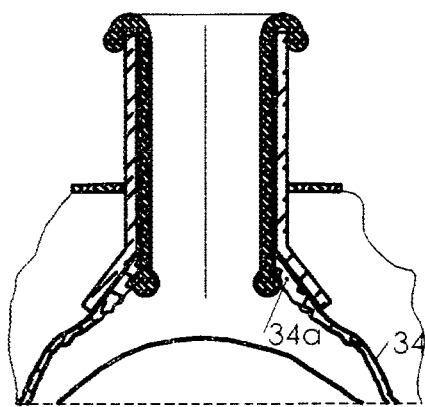
FIG. 10d shows a sealed pericardial opening.

FIG. 10d shows a sealed pericardial opening 34a. Between a soft tissue retractor 291 and a cone 70a, pericardium 34 is clamped, preventing fluid flows, especially gas flows (not shown), that gaps are closed (not shown).

FIG. 11 shows a schematic diagram of the positions of an implant.

FIG. 11a shows a layer of an implant 150 within the device 10. The implant 150 is connected to an implant guide 154. In the preferred embodiment, an implant guide is provided between implant 150 and implant guide 154 as a fracture site 155. Alternatively, this may be broken by wobbling or turning it more strongly so that implant 150 is separated from implant guide 154.

In a preferred embodiment, a passage through the implant 150, the fracture site 155 and the implant guide 154 has been worked out. Compressed air or fluid may be introduced into or removed from the implant 150 through this passage.

In a preferred embodiment, a guide wire 240 is passed through the continuous passage, which is connected to the implant 150 in at least one location. The connection point may be a knot, a welding point or an adhesive point. Because the guide wire 240 is attached to the implant 150, the implant may be guided through the guide wire 240.

In a preferred embodiment, the implant 150 is a cushion 153, whose volume may be changed over time by adding and removing compressed air. Alternatively, a gas may be used.

Alternatively, a guide wire 240 may be inserted through the device tunnel 19, which is attached to the outside of implant 150.

By means of the guide wire 240, the implant 150 may be advanced in the direction of the heart 31 up to the pericardium 34

FIG. 11b shows a position of an implant 150 within the device or any other tubular guide structure. The implant 150 is alternatively advanced through the device tunnel 19 in the direction of the pericardium 34 by a guide wire (see FIG. 11a) or by an implant guide (not shown).

FIG. 11c shows an alternative position of an implant 150 compared to FIG. 11b for its temporary support. For this purpose, the pericardium 34 is opened so that implant 150 may be advanced through a pericardial opening.

The object is to insert the implant 150 as deeply as possible into the pericardium 34. This object is solved by a method in which an implant anchor 310 is inserted and fixed in the pericardium 34.

The method comprises the steps of opening skin (not shown), advancing a device through the opening to the pericardium 34, grasping and opening the pericardium 34, advancing an implant anchor 310 through the device and through the pericardial opening 34a and placing it between an inner side of the pericardium 34, between the pericardium 34 and the heart 31, returning at least one guide wire 320 and passing it through a passage of an implant 150, and advancing the implant 150 along the guide wire 320 through a device tunnel 19 of guide wire 320 to implant anchor 310.

It is advantageous to position at least one implant 150 securely between the heart 31 and pericardium 34 so that an implant 150 may be placed at a predefined location.

In a preferred embodiment, a fluid column is used as the diaphragmatic seal of implant 150. This solves the object of transmitting pressure changes almost immediately. If the heartbeat is measured in the implant at the same time, the support of the heart may be optimally controlled by a computer-aided control system.

The embodiment shown in FIG. 11c may also be used independently of other embodiments.

Figure 11D:
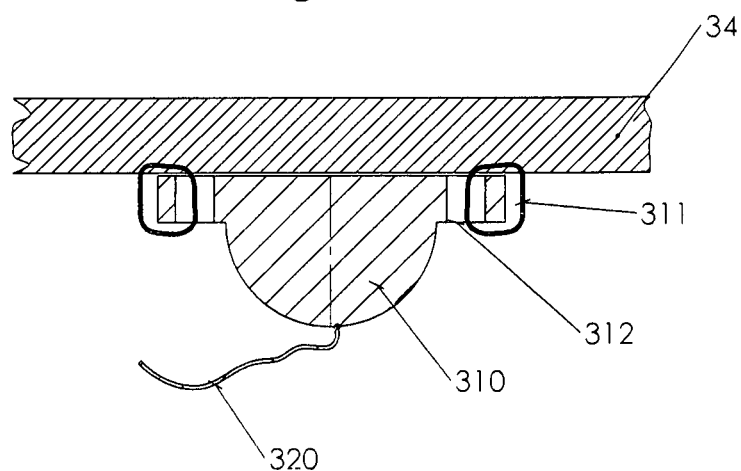
FIG. 11d shows a detail with an implant anchor.

FIG. 11d shows a detailed view with an implant anchor 310.

Implant anchor 310 is sutured to the pericardium 34 with at least one cord 311 and at least one eyelet 312. In a particularly advantageous embodiment, the implant anchor 310 is sutured to the pericardium 34 on its circumference by means of a plurality of eyelets 312. A guide wire 320 is attached to it.

Figure 11E:
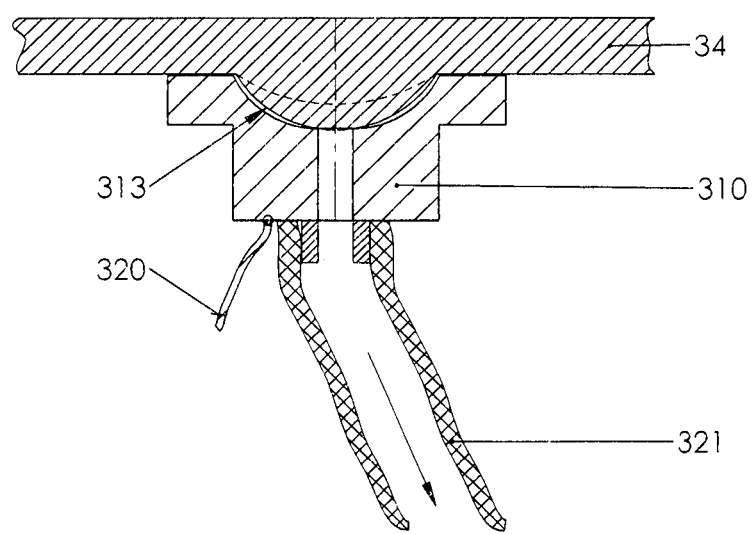
FIG. 11e shows a detail with an implant anchor.

FIG. 11e shows a detail with an implant anchor 310, which is sucked to the pericardium 34 by means of negative pressure. For doing that, a guide suction hose 321 is flanged to the implant anchor 310 so that air or fluid from at least one implant dome 313 in the implant anchor 310 may be conveyed, e.g. pumped. This has the advantage that the implant anchor 310 is sucked up to the pericardium 34. A guide wire 320 or a guide cable (not shown) or a guide cord (not shown) may be additionally attached to the implant anchor 310.

LIST OF REFERENCE NUMBERS

10 Device
12 proximal device end
13 Fixture tip
15 Axial direction
16 Volume
19 Device tunnel
20 ring grippers
31 Heart
32 Tip of the heart
33 Heart
34 Pericardium
34a Pericardial opening
35 Inner pericardium
36 Internal pressure of pericardial bag
37 Skin
37a Insertion opening
39 Interior volume
40 Outer part
41 Outer part component end
42 Outer part end length
43 Outer part end section
44 Outer part end surface
50 Outer tube
51 Outer diameter of the outer tube
52 Inner diameter of the outer tube
53 Outer tube end
54 Outer tube end surface
56 Outer tube collar
59 Outer tube end surface profile
59a Outer tube end surface notches
60 Outer knurling wheel
61 Rotation direction outer knurl wheel
70 Inner tube
70a Cone
71 Outer diameter of the inner tube
72 Inner diameter of the inner tube
74 Inner tube end surface
76 Inner tube collar
78 Inner tube end surface profile
80 Inner knurling wheel
81 Direction of rotation inner knurling wheel
90 Inner part 93 Inner part collar
94 Inner part collar diameter
100 Pin
101 Outer pin diameter
102 Through-hole
103 Through-hole diameter
104 Pin collar
105 pin tip
106 Pin hole
107 Pin hole diameter
108 Pin knob
109 Pin length
110 Probes
111 Probe shaft
112 Probe head
120 Spring element
130 Safety device
131 Safety groove
132 retaining ring
150 Implant
153 Pillow
154 Implant guide
155 Implant guide fracture site
200 Human body
201 Body access opening
202 penetration depth
203 Working depth
220 tine
220a Serrated gripper
220b serrated gripper shank
221 Serrated centre line
222 Tine pocket
223 Angle of attack
224 Freewheel
225 Gripping direction
230 Groove gripper
231.1 Outer tube groove
231.2 Inner tube groove
233.3 Internal part groove gripper
240 Guide wire
250 Puncture needle
260 Vacuum pump
261 Flange
270 Mechanical mechanism
271 Nut
272 Spacers
273 Apical spacer end
280 sealing
281 stuffing box
290 Support structure
291 soft tissue retractor
292 Apical clamping ring
293 Ventral clamping ring
294 locking shoulder
300 Gas flow
301 Slit
310 Implant anchor
311 Cord
312 eyelet
313 implant dome
320 Guide wire
321 Guide suction hose

The invention claimed is:

1. A method for gripping the pericardium of a patient, comprising:
providing a device having an outer part and an inner part, wherein the outer part includes an inner tube movably arranged in an outer tube,
the inner tube having an inner tube diameter and an inner tube end with an inner tube end surface with a first surface structure; and
the outer tube having an outer tube diameter, the outer tube diameter being larger than the inner tube diameter, and an outer tube end with an outer tube end surface with a second surface structure, the first surface structure and the second surface structure being formed differently;
wherein the inner tube is movably arranged in the outer tube, wherein the inner tube is rotatably arranged in the outer tube;
creating a body opening;
advancing the device through the body opening in the direction of the pericardium;
touching the pericardium, the heart or a layer arranged on the heart with at least one end of the device;
moving the outer part until the outer tube end surface and the inner tube end surface are arranged flush with each other on the pericardium;
moving the inner part within the inner tube; and
gripping the pericardium by turning the inner tube in relation to the outer tube.

2. The method according to claim 1, further comprising mechanically lifting the pericardium from the heart by the device.

3. The method according to claim 1, further comprising removing the inner part from the device.

4. Method according to claim 1, further comprising inserting a tool into the heart through the device.

5. The method according to claim 1, further comprising generating a signal by the device.

6. The method according to claim 1, further comprising gripping at least one tooth.

7. A device for grasping the pericardium of a patient, comprising:
an inner tube having an inner tube diameter and an inner tube end with an inner tube end surface with a first surface structure;
an outer tube having an outer tube diameter, the outer tube diameter being larger than the inner tube diameter, and an outer tube end with an outer tube end surface with a second surface structure, the first surface structure and the second surface structure being formed differently; and
an inner part, the inner part being movably arranged in the inner tube,
wherein the inner tube is movably arranged in the outer tube,
wherein the inner tube is rotatably arranged in the outer tube, and
wherein gripping the pericardium is effected by arranging the outer tube end surface and the inner tube end surface flush with each other while touching the pericardium and turning the inner tube in relation to the outer tube.

8. The device according to claim 7, further comprising a sensor probe in at least one through-bore of the inner part.

9. The device according to claim 7, further comprising a spring element arranged between a surface of the inner part and a surface of a sensor probe head.

10. The device according to claim 7, wherein at least one of the inner tube or the outer tube is flexible.

11. The device according to claim 7, wherein at least one of the inner tube or the outer tube is a hose.

12. The device according to claim 7,
wherein the inner tube end surface is annular and
wherein the outer tube end surface is annular.

13. The device according to claim 7,
wherein an end shoulder is formed in the outer tube at the outer tube end or in the inner tube at the inner tube end.

14. The device according to claim 7,
wherein the inner tube end surface and the outer tube end surface cooperate to grasp the same side of the pericardium.

\* \* \* \* \*